(12) United States Patent
Curran et al.

(10) Patent No.: US 8,415,307 B1
(45) Date of Patent: Apr. 9, 2013

(54) ANTIBIOTIC COMPOSITIONS FOR THE TREATMENT OF GRAM NEGATIVE INFECTIONS

(75) Inventors: William V. Curran, Pear River, NY (US); Christopher M. Liu, Somerville, MA (US); Amy C. D. Bombardier, Waltham, MA (US); Richard A. Leese, Suffern, NY (US); You Seok Hwang, Concord, MA (US); Blaise S. Lippa, Acton, MA (US); Yanzhi Zhang, East Walpole, MA (US)

(73) Assignees: BioSource Pharm, Inc., Spring Valley, New York, NY (US); Cubist Pharmaceuticals, Inc., Lexington, MA (US)

(*) Notice: Subject to any disclaimer, the term of this patent is extended or adjusted under 35 U.S.C. 154(b) by 5 days.

(21) Appl. No.: 13/167,495

(22) Filed: Jun. 23, 2011

Related U.S. Application Data

(60) Provisional application No. 61/382,270, filed on Sep. 13, 2010, provisional application No. 61/357,979, filed on Jun. 23, 2010.

(51) Int. Cl.
*A61K 38/08* (2006.01)

(52) U.S. Cl.
USPC ............ 514/21.6; 530/319; 930/190; 514/2.2; 514/2.3; 514/2.8; 514/3.6

(58) Field of Classification Search .................. None
See application file for complete search history.

(56) References Cited

U.S. PATENT DOCUMENTS

| | | | |
|---|---|---|---|
| 3,753,970 | A | 8/1973 | Bouchaudon et al. |
| 3,854,480 | A | 12/1974 | Zaffaroni |
| 4,091,092 | A | 5/1978 | Parker et al. |
| 4,399,067 | A | 8/1983 | Debono |
| 4,452,775 | A | 6/1984 | Kent |
| 4,482,487 | A | 11/1984 | Abbott et al. |
| 4,524,135 | A | 6/1985 | Abbott et al. |
| 4,537,717 | A | 8/1985 | Abbott et al. |
| RE32,310 | E | 12/1986 | Debono |
| RE32,311 | E | 12/1986 | Debono |
| 5,028,590 | A | 7/1991 | Fukuda et al. |
| 5,039,789 | A | 8/1991 | Fukuda et al. |
| 5,041,567 | A | 8/1991 | Rogers et al. |
| 5,239,660 | A | 8/1993 | Ooi |
| 6,380,356 | B1 | 4/2002 | Griffin et al. |
| 6,511,962 | B1 | 1/2003 | Borders et al. |
| 2001/0021697 | A1 | 9/2001 | Lowenstein et al. |
| 2003/0224475 | A1 | 12/2003 | Leese et al. |
| 2008/0207874 | A1* | 8/2008 | Leese et al. ............ 530/317 |
| 2008/0279820 | A1 | 11/2008 | Hicks et al. |
| 2010/0160215 | A1 | 6/2010 | Leese |

FOREIGN PATENT DOCUMENTS

| | | |
|---|---|---|
| JP | 2003-505042 | 2/2003 |
| WO | WO 95-05384 | 2/1995 |
| WO | WO 01-05815 | 1/2001 |
| WO | WO 01-44271 | 6/2001 |
| WO | WO 01-44272 | 6/2001 |
| WO | WO 01-44274 | 6/2001 |
| WO | WO 02-05837 A1 | 1/2002 |
| WO | WO 02-055543 A2 | 7/2002 |
| WO | WO 03-014147 | 2/2003 |
| WO | WO 2006-083317 A2 | 8/2006 |
| WO | WO 2010-075416 A1 | 7/2010 |

OTHER PUBLICATIONS

Barnett, M. et al., "Sodium Sulphomethyl Derivatives of Polymyxins," *Br. J. Pharmacol.* 23:552-574 (1964).

Barrett, et al. "Edman Stepwise degradation of polypeptides: a new strategy employing mild basic cleavage conditions," *Tetrahedron Letters* 26(36):4375-4378 (1985).

Berendsen, H. J., "A Glimpse of the Holy Grail?," *Science*, 282: 642-643 (Oct. 1998).

Berge, et al., "Pharmaceutical Salts," *J. Pharm. Sci.* 66(1):1-19 (1977).

Boeck, et al., "Deacylation of A21978C, an acidic Lipopeptide Antibiotic Complex, by *Actinoplanes utahensis*," *J. Antibiot.* 41(8): 1085-1092 (1988).

Boeck, et al., "Deacylation of Echinocandin B by *Actinoplanes utahensis*," *J. Antibiot.* 42(3):382-388 (1989).

Bradley, C., et al., "Limits of Cooperativity in a Structurally Modular Protein: Response of the Notch Ankyrin Domain to Analogous Alanine Substitutions in Each Repeat," *J. Mol. Biol.*, 324: 373-386 (2002).

Brandt, et al., "Abnormal behaviour of proline in the isothiocyanate degradation," *Physiol. Chem.*, 357:1505-1508 (1976).

Brownlee, G., et al., "Comparative Biological Studies of Polymyxin A and Polymixin D," *Annals New York Academy of Sciences*, 51(5): pp. 891-896 (Jun. 1949).

Brownlee, G., et al., "The Pharmacology of Polymyxin A, B, and D," *Annals New York Academy of Sciences*, 51(5): pp. 952-967 (Jun. 1949).

Brownlee, G., et al., "Remarks on Clinical Results with Polymyxin A and B," *Annals New York Academy of Sciences*, 51(5): pp. 998-1000 (Jun. 1949).

Bryer, M., et al., "Pharmacology of Polymyxin," *Annals New York Academy of Sciences*, 51(5): pp. 935-943 (Jun. 1949).

Catch, J.R., et al., "The Chemistry of Polymyxin A," *The Wellcome Chemical Research Laboratories*, 51(5): pp. 917-923 (Jun. 1949).

(Continued)

*Primary Examiner* — Anish Gupta
*Assistant Examiner* — Randall L Beane
(74) *Attorney, Agent, or Firm* — Hamilton, Brook, Smith & Reynolds, P.C.

(57) ABSTRACT

Provided herein are novel compounds and novel protected compounds that can be derived from polymyxin, including, e.g., polymyxin A. The novel compounds have antibacterial properties against a diverse range of Gram negative bacteria and reduced toxicity compared to polymyxins such as polymyxin A. Also provided are antibacterial pharmaceutical compositions containing the novel compounds and novel protected compounds, as well as methods for preparing the antibacterial compounds and protected compounds.

13 Claims, 1 Drawing Sheet

OTHER PUBLICATIONS

Bruch, M., et al., "Higher-Order Structure of Polymyxin B: The Functional Significance of Topological Flexibility," *J. Am.Chem. Soc.* 121: 11993-12001 (1999).

Castanheira, M. et al., "Antimicrobial susceptibility patterns of KPC-producing or CTX-M-producing Enterobacteriaceae," *Microb. Drug Resist*.16:61-65 (2010).

Chihara, et al., "Chemical Synthesis and Characterization of α-N-Octanoyl and Other α-N-Acyl Colistin Nonapeptide Derivatives," *Agr. Biol. Chem.*, 37(12): 2709-2717 (1973).

Chihara, et al., "Chemical Synthesis and Characterization of n-Fattyacyl Mono-Aminoacyl Derivatives of Colistin Nonapeptide," *Agr. Biol. Chem.*, 38(10): 1767-1777 (1974).

Chihara, et al., "Chemical synthesis, isolation, and characterization of α-N-fattyacyl colistin nonapeptide with special reference to the correlation between antimicrobial activity and carbon number off fattyacyl moiety," *Agr. Biol. Chem.*, 38(3): 521-529 (1974).

Choi, et al. "Identification of a Polymyxin Synthetase Gene Cluster of *Paenibacillus polymyxa* and Heterologous Expression of the Gene in *Bacillus subtillis*," *Journal of Bacteriology*, 191(10): 3350-3358 (May 2009).

Clausell, A. et al., "Membrane Association and Contact Formation by a SynthetiC Analogue of Polymyxin B and Its Fluorescent Derivatives," *J. Phys. Chem. B* 110:4465-4471 (2006).

Clausell, A. et al., "Synthesis and Membrane Action of Polymyxin B Analogues," *Luminescence* 20: 117-123 (2005).

Clinical and Laboratory Standards Institute, M07-A8, "Methods for dilution antimicrobial susceptibility tests for bacteria that grow aerobically," approved standard: eighth edition, Wayne, PA: CLSI (2009).

Clinical and Laboratory Standards Institute, M1 00-S20-U, "Performance standards for antimicrobial susceptibility testing," 20th informational supplement, Wayne, PA: CLSI (2010).

"Designing Custom Peptides," from SIGMA Genosys, pp. 1-2; http:--www.sigma-genosys.com-peptide_design.asp, retrieved from the internet on Dec. 16, 2004.

De Visser, et al., "Solid-phase synthesis of polymyxin B1 and analogues via a safety-catch approach" *J. Pept. Res.*, 61:298-306 (2003).

Duwe, et al., "In Vitro Cytotoxicity and Antibiotic Activity of Polymyxin B Nonapeptide," *Antimicrob. Agents Chemotherapy*, 30:340-341 (1986).

Elverdam, et al., "Isolation and Characterization of Three New Polymyxins in Polymyxins B and E by High-Performance Liquid Chromatography," *J. Chromatography*, 218: 653-661 (1981).

Evans, et al., "Polymyxin B Sulfate and Colistin: Old Antibiotics for Emerging Multiresistant Gram-Negative Bacteria," *Annals of Pharmacotherapy*, 33:960-967 (1999).

Extended European Search Report for EP Application No. 10184953.7 dated Apr. 6, 2011.

Falagas, et al., "Colistin: The Revival of Polymyxins for the Management of Multidrug-Resistant Gram-Negative Bacterial Infections," *Rev. Anti-Infect. Agents*. 40: 1333-1341 (2005); Erratum *Rev. Anti-Infect. Agents* 42: 1819 (2006).

Fostel, et al., "Emerging novel antifungal agent," *Drug Discovery Today* 5:25-32 (2000).

Frecer, V. et al., "Dc Novo Design of Potent Antimicrobial Peptides," *Antimicrob. Agents Chemother*. 48(9):3349-3357 (2004).

Gales, AC. et al., "Global assessment of the antimicrobial activity of polymyxin B against 54 731 clinical isolates of Gram-negative *Bacilli*,": report from the SENTRY antimicrobial surveillance programme (20012004), *Clin Microbiol Infect* 12:315-321 (2006).

Gershonov, et al., "A Novel Approach for a Water-Soluble Long-Acting Insulin ProDrug: Design, Preparation, and Analysis of [(2-Sulfo)-9-Fluorenylmethoxycarbonylh-Insulin," *J. Med. Chem.* 43(13):2530-2537 (2000).

Giamarellou, H. et al., "Multidrug-resistant Gram-negative infections: What are the treatment options?," Drugs 69: 1879-1901 (2009).

Han, et al., "Current developments in stepwise Edman degradation of peptides and proteins," *Int. J. Biochem.* 17(4):429-445 (1985).

Han, et al., "Dégradation récurrente d'Edman," *Biochimie* 59:557-576 (1977).

Hausmann, et al., "Polymyxin B1. Fractionation, molecular weight determination, amino acid and fatty acid composition," *J. Am. Chem. Soc*. 76:4892-4896 (1954).

International Preliminary Report on Patentability for International Application No. PCT-US2005-023343 dated Jan. 9, 2007.

International Preliminary Report on Patentability for International Application No. PCT-US2009-069247 dated Jul. 7, 2011.

Notification of Transmittal of International Search Report and the Written Opinion of the International Searching Authority, or the Declaration of International Application No. PCT-US2005-023343 dated Dec. 6, 2006.

International Search Report mailed May 6, 2010, for International Patent Application No. PCT-US2009-069247.

Jarolmen, et al., "Activity of Minocycline Against R-Factor Carrying *Enterobacteriaceae*," *Infect. Immun*. 1(4):321-326 (1970).

Kanazawa, K. et al., "Contribution of Each Amino Acid Residue in Polymyxin B3 to Antimicrobial and Lipopolysaccharide Binding Activity," *Chem. Pharm. Bull*. 57(3):240-244 (2009).

Kato, et al., "The Structure of Octapeptin D (Studies on Antibiotics from the Genus *Bacillus*. XXVIII)," *J. Antibiotics* 33(2): 186-191 (Feb 1980).

Katsuma, N. et al., "Development of Des-Fatty Acyl-Polymyxin B Decapeptide Analogs with *Pseudomonal aeruginosa-Specific* Antimicrobial Activity," *Chem. Pharm. Bull*. 57(4):332-336 (2009).

Katz, M., et al., "Lipid binding and membrane penetration of polymyxin B derivatives studied in a biomimetic vesicle system," *Biochem J.*, 375: 405-413 (2003).

Kimura, et al., "Polymyxin acylase: purification and characterization, with special reference to broad substrate specificity," *Agric. Biol. Chem.*, 53(2):497-504 (1989).

Kimura, et al., "Polymyxin B Octapeptide and Polymyxin B Heptapeptide are Potent Outer Membrane Permeability-Increasing Agents," *J. Antibiot.*, 45:742-749 (1992).

Kimura, et al., "Polymyxin P, New Antibiotics of Polymyxin Group," *J. Antibiot.*, XXII(9): 449-450 (Sep. 1969).

Kleinkauf, H. et al., "Nonribosomal biosynthesis of peptide antibiotics," *Eur. J. Biochem.*, 192:1-15 (1990).

Kline, et al., "Synthesis and characterization of the colistin peptide polymyxin E1 and related antimicrobial peptides," *J. Peptide Res.*, 57(3):175-187 (2001).

Kreuzman, et al., "Membrane-associated echinocandin B deacylase of *Actinoplanes utahensis*: purification, characterization, heterologous cloning and enzymatic deacylation reaction," *J. Ind. Microbiol. Biotechnol*. 24:173-180 (2000).

Kristensen, H.K. et al., "Separation of Polymyxins by Micellar Electrokinetic Capillary Chromatography," *J. Chromatography* 628:309-315 (1993).

Kurihara, et al., "Studies on the compounds related to colistin. V. Synthesis and pharmacological activity of colistin analogues," *Yakugaku Zasshi*, 92: 129-134 (1972).

Liu et al., "A novel fmoc-based anchorage for the synthesis of protected peptide on solid phase," *Int. J. Pept. Protein Res*. 35:95-98 (1990).

Li, C. et al., "Incremental Conversion of Outer-Membrane Permeabilizers into Potent Antibiotics for Gram-Negative Bacteria," *J. Am. Chem. Soc*. 121:931-940 (1999).

Li, J. et al., "Colistin: The re-emerging antibiotic for multidrug resistant Gram-negative bacterial infections," Lancet Infect Dis 6:589-601 (2006).

Livermore, D.M., "Has the era of untreatable infections arrived?,"*J Antimcrob. Chemother*, 64 Suppl, 1 :i29i36 (2009).

Mares, J., et al., "Interactions of Lipopolysaccharide and Polymyxin Studied by NMR Spectroscopy," *J. Biol. Chem.*, 284(17): 11498-11506 (Apr. 24, 2009).

Markou, et al., "Intravenous colistin in the treatment of sepsis from multiresistant Gramnegative *bacilli* in critically ill patients," *Critical Care*, 7:R78-R83 (2003).

Martin, et al., "Isolation, structural characterization, and properties of mattacin (polymyxin M), a cyclic peptide antibiotic produced by *Paenibacillus kobensis M,*" *J. Bio. Chem.*, 278(15):13124-13132 (2003).

Matsenaga, H., et al., "Polymyxin P, Antibiotics from *Bacillus polymyxa* T-39; Fermentation, Isolation, Structure Elucidation and Antibacterial Activity," *Mukogawa Women's University* Nishimoyia 663, 37: 37-43 (1995).

McCallister, et al., "Antimicrobial properties of liposomal polymyxin B," *J. Antimicrob. Chemother.*, 43:203-210 (1999).

Merrifield, et al., "9-(2-sulfo)fluorenylmethyloxycarbonyl chloride, a new reagent for the purification of synthetic peptides," *J. Org. Chem.*, 43(25):4808-4816 (1978).

Michalopoulos, A. et al., "Colistin and polymyxin B in critical care," *Crit Care Clin* 24: 377-391 (2008).

Molina, J. et al., "New Information about the Polymyxin-Colistin Class of Antibiotics," *Expert Opin. Pharmacother.* 10(17):2811-2828 (2009).

Mutter et al., "A New Base-Labile Anchoring Group for Polymer-Supported Peptide Synthesis," *Helv. Chim. Acta.* 67:2009 (1984).

Nakajima, "Structure-activity relationship of colistins," *Chem. Pharm. Bull.*, 15(8): 1219-1224 (1967).

Ngo, J., et al., "Computational Complexity, Protein Structure Prediction, and the Levinthal Paradox," *The Protein Folding Problem and Tertiary Structure Prediction*, pp. 491-495, (1994).

Non Final Office Action for U.S. Appl. No. 11/630,847 dated Mar. 3, 2011.

O'Dowd, H. et al., "Preparation of Tetra-Boc-Protected Polymyxin B Nonapeptide," *Tetrahedron Lett.* 48:2003-2005 (2007).

Ohki, K., et al., "Synthesis and Antimicrobial Activity of Polymyxin B Component Peptides," *Peptide Science*, p. 189-192 (2002).

Okimura, K. et al., "Chemical Conversion of Natural Polymyxin B and Colistin to Their N-Terminal Derivatives," *Bull. Chem. Soc. Jpn.* 80(3):543-552 (2007).

Okimura, K. et al., "Semi-synthesis of Polymyxin B (2-10) and Colistin (2-10) Analogs Employing the Trichloroethoxycarbonyl (Troc) Group for Side Chain Protection of α, γ-Diaminobutyric Acid Residues," *Chem. Pharm. Bull.* 55(12):1724-1730 (2007).

Orwa, J.A. et al., "Isolation and Structural Characterization of Colistin Components," *J. Antibiotics* 54(7):595-599 (2001).

Orwa, J.A. et al., "Isolation and Structural Characterization of Polymyxin B Components," *J. Chromatography A* 912:369-373 (2001).

Parker, et al., "EM49: A New Peptide Antibiotic IV. The Structure of EM49," *J. Antibiot.*, 28(5):379-389 (1975).

Parker, et al., "EM49: A New Peptide Antibiotic II. Chemical Characterization," *J. Antibiot.*, 26(8):449-456 (1975).

Pristovsek, P., et al., "Solution Structure of Polymyxins B and E and Effect of Binding to Lipopolysaccharide: An NMR and Molecular Modeling Study," *J. Med. Chem.* 42: 4604-4613 (1999).

Puar, M.S., "Carbon-13 NMR Studies of EM49 and Related Octapeptins," *J. Antibiotics* 33:760-763 (1980).

Rosenthal, K.S., et al., "Mechanism of Action of EM 49, Membrane-Active Peptide Antibiotic," *Antimicrob. Agents Chemother.* 12(6):665-672 (1977).

Rudinger, J., "Characteristics of the amino acids as components of a peptide hormone sequence," *Peptide Hormones*, J. Parsons Edition, University Park Press, pp. 1-7 (Jun. 1976).

Rustici, A., et al., "Molecular Mapping and Detoxification of the Lipid A Binding Site by Synthetic Peptides," *Science* 259:361-365 (1993).

Sader, H.S., et al., "Assessment of colistin and polymyxin B antimicrobial susceptibility testing methods against non-fermentative Gram-negative *bacilli* (NFGNB)," Abstr. C173, 106th ASM, Orlando FL (2006).

Sakura, et al., "The Contribution of the N-Terminal Structure of Polymyxin B Peptides to Antimicrobial and Lipopolysaccharide Binding Activity" *Bull. Chem. Soc. Jpn.*, 77: 1915-1924 (2004).

Salem, et al., "Synthesis of Pelargonoyl-Cyclic Decapeptide Analog of the Antibiotic Polymyxin B1," *Pharmazie*, 35:540-541 (1980).

Schechter, et al., "N-[(2-Sulfo)-9-Fluorenylmethoxycarbonylh-gentamicin $C_1$ is a Long-Acting Prodrug Derivative," *J. Med. Chem.*, 45:4264-4270 (2002).

Schechter, et al., "Prolonging the half-life of human interferon-α2 in circulation: Design, preparation, and analysis of (2-sulfo-9-fluorenylmethoxycarbonylh-interferon-α2," *Proc. Nat. Acad. Sci., U.S.A.*, 98(3): 1212-1217 (2001).

Schechter, et al., "Suspensions of pro-drug insulin greatly prolong normoglycemic patterns in diabetic rats," *Biochem. Biophys. Res. Commun.*, 307:315-321 (2003).

Schinzel, P., et al. "The phosphate recognition site of *Escherichia coli* maltodextrin phosphorylase," *Federation of European Biochemical Societies*, 286(1,2): 125-128 (Jul. 1991).

Shoji, J. et al., "Isolation of Two New Polymyxin Group Antibiotics (Studies on Antibiotics from the Genus *Bacillus*. XX)," *J. Antibiot.* 30:1029-1034 (1977).

Shoji, J. et al., "The Structure of Polymyxin $S_i$ (Studies on Antibiotics from the Genus *Bacillus*. XXI)," *J. Antibiot.* 30(12):1035-1041 (1977).

Shoji, J. et al., "The Structure of Polymyxin T (Studies on Antibiotics from the Genus *Bacillus*. XXII)," *J. Antibiot.* 30(12):1042-1048 (1977).

Short, E., "Mechanism of Methionine Protection Against the Nephrotoxicity of Polymyxin A," *Brit. J. Pharmacol.*, 7 248-254 (1952).

Sil, D. et al., "Bound to Shock: Protection from Lethal Endotoxemic Shock by a Novel, Nontoxic, Alkylpolyamine Lipopolysaccharide Sequestrant," *Antimicrob. Agents Chemother.* Published online ahead of print on Jun. 4, 2007, pp. 1-32; retrieved from the Internet at www.aac.asm.org on Dec. 1, 2009.

Srinivasa, B.R. et al., "Chemical Modification of Peptide Antibiotics: Part VI—Biological Activity of Derivatives of Polymyxin B," *Indian J. Biochem. Biophys.* 14:54-58 (1978).

Srinivasa, et al., "Essential Amino Groups of Polymyxin B," *Indian J. Biochem. Biophys,.*17:112-118 (1980).

Storm, et al., "Polymixin and related peptide antibiotics," *Ann. Rev. Biochem.*, 46:723-763 (1977).

Sugawara, K. et al., "Bu-2470, a New Peptide Antibiotic Complex. II. Structure Determination of Bu-2470 A, B1, B2a and B2b," *J. Antibiot.* 36:634-638 (1983).

Takeshima, et al., "A deacylation enzyme for Aculeacin A, a neutral lipopeptide antibiotic, from Actinoplanes utahensis: purification and characterization," *J. Biochem.*, 105:606-610 (1989).

Tarr, "Improved manual sequencing methods," *Methods Enzymol.*, 47:335-357 (1977).

Trakhanova, M.N., et al., "Structural and Functional Investigation of Polymyxins, Structure and Biological Properties of Polymyxin M Analogs," *All Union Research Institute of Antibiotics*, Moscow, 1: 20-24 (1989) (English Abstract on p. 24).

Trakhanova, M.N., et al., "Structural and Functional Investigation of Polymyxins, Isolation and Properties of Individual Polymyxin M Components," *All Union Research Institute of Antibiotics*, Moscow, 4: 262-266 (1988) (English Abstract is on p. 266).

Tsubery, et al., "N-Terminal Modifications of Polymyxin B Nonapeptide and Their Effect on Antibacterial Activity," *Peptides*, 22: 1675-1681 (2001).

Tsubery, H., et al., "Neopeptide Antibiotics That Function as Opsonins and Membrane-Permeabilizing Agents for Gram-Negative Bacteria," *Antimicrob. Agents Chemother*. 49(8):3122-3128 (2005).

Tsubery, H., et al., "Structure-Function Studies of Polymyxin B Nonapeptide: Implications to Sensitization of Gram-Negative Bacteria," *J. Med. Chem.* 43:3085-3092 (2000).

Tsubery, H., et al., "Modulation of the Hydrophobic Domain of Polymyxin B Nonapeptide: Effect on Outer-Membrane Permeabilization and Lipopolysaccharide Neutralization," *Mol. Pharmacol.* 62(5):1036-1042 (2002).

Tueber, M., "Preparation of biologically active mono-N-acetyl($^{14}$C)-derivatives of the membrane-specific polypeptide antibiotic polymyxin B," *Z. Naturfbrsch.* 25b: 117 (1970).

Tygacil Package Insert, available at www.wyeth.com, accessed Aug. 2009 (2009).

Vaara, M., "The Outer Membrane Permeability-Increasing Action of Linear Analogues of Polymyxin B Nonapeptide," *Drugs Exptl. Clin. Res.* 17(9):437-444 (1991).

Vaara, M., et al., "Novel Polymyxin Derivatives Carrying Only Three Positive Charges Are Effective Antibacterial Agents," *Antirnicrob. Agents Chemother*. Published online ahead of print on Jun. 30, 2008, pp. 1-31; retrieved from the Internet at www.aac.asm.org on Dec. 1, 2009.

Velkov, T., et al., "Structure-Activity Relationships of Polymyxin Antibiotics," *J. Med. Chem*, 53(5): 1898-1916 (2010).

Voet, D., et al., "Abnormal Hemoglobins," *Biochemistry Second Edition*, pp. 235-241 (1995).

Vogler, K. et al., "The Chemistry of the Polymyxin Antibiotics," *Experientia* 22(6):345416 (1966).

Wang, W., et al., "Structure and Dynamics of $^{13}$C,$^{15}$N-Labeled Lipopolysaccharides in a Membrane Mimetic," *Angew. Chem. Int. Ed.*, 47: 9870-9874 (2008).

Weinstein, et al., "Selective Chemical Modifications of Polymyxin B," *Biorg. Med. Chem. Lett.*, 8:3991-3996 (1988).

Wilkinson, S., et al., "Structures of the Polymyxins A and the Question of Identity with the Polymyxins M," Nature, No. 5059 p. 311 (Oct. 15, 1966).

Written Opinion of the International Searching Authority for International Application No. PCT-US2005-023343 dated Dec. 6, 2006.

Written Opinion of the International Searching Authority for International Application No. PCT-US2009-069247 dated Jun. 23, 2011.

Witzke, N.M. et al., "Broad-Spectrum Derivatives of Polymyxin B and Colistin," *J. Antibiot.* 29(12):1349-1350 (1976).

Zavascki, a.P., et al., "Polymyxin B for the treatment of multidrug-resistant pathogens: Antimicrob Chemother 60: 1206-1215 (2007) A critical review," *J. Antimicrob. Chemotherapy*, 60: 1206-1215 (2007).

Notice of Allowance for U.S. Appl. No. 11/630,847 dated Aug. 18, 2011.

Non Final Office Action for U.S. Appl. No. 12/644,943, titled: "Antibiotic Compositions for the Treatment of Gram Negative Infections", dated Feb. 21, 2012.

Notice of Allowance for U.S. Appl. 12/644,943, titled: "Antibiotic Compositions for the Treatment of Gram Negative Infections" dated Aug. 31, 2012.

* cited by examiner

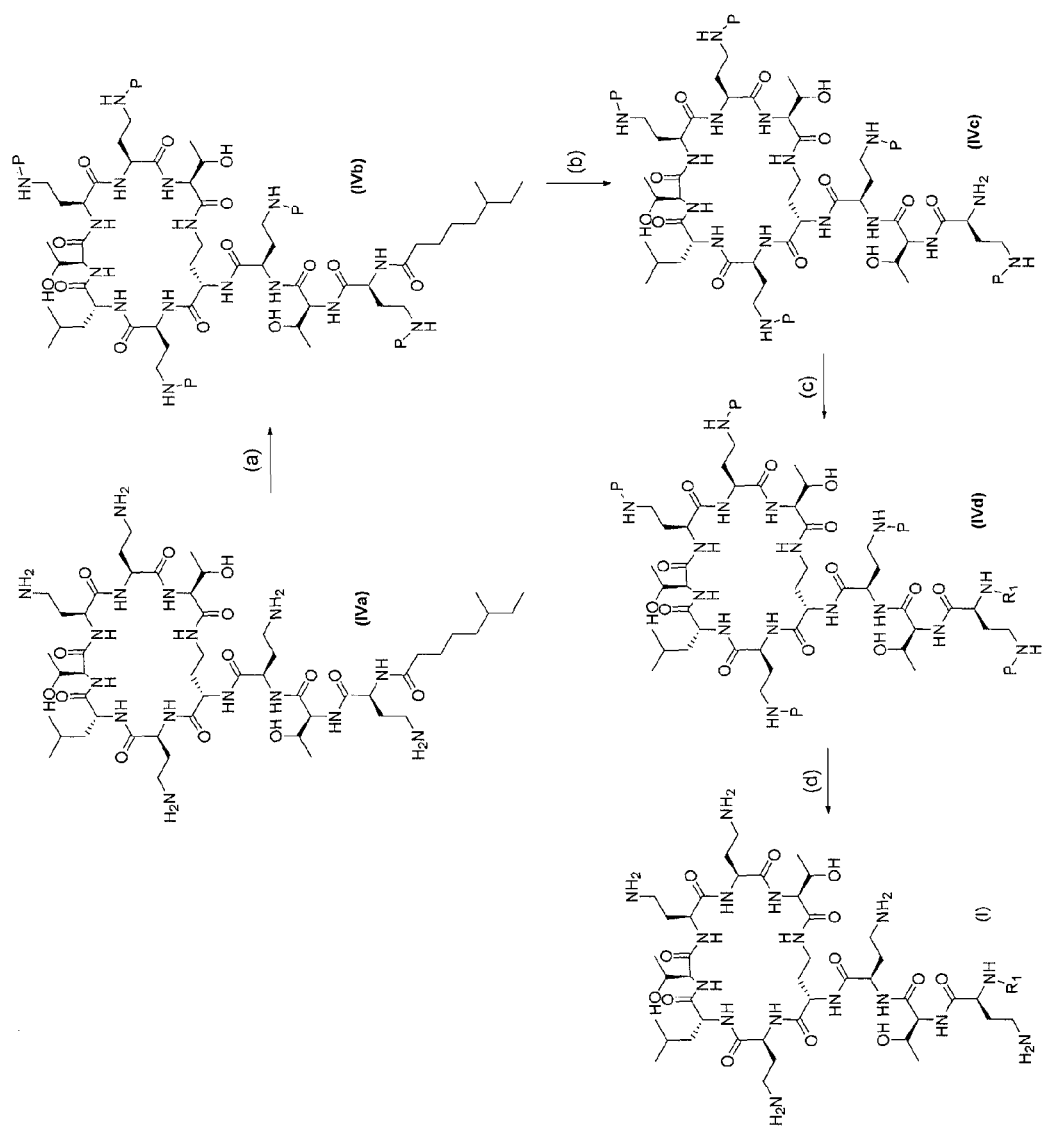

ANTIBIOTIC COMPOSITIONS FOR THE TREATMENT OF GRAM NEGATIVE INFECTIONS

RELATED APPLICATIONS

This application claims the benefit of U.S. Provisional Application No. 61/382,270, filed on Sep. 13, 2010, and U.S. Provisional Application No. 61/357,979, filed on Jun. 23, 2010.

The entire teachings of the above applications are incorporated herein by reference.

BACKGROUND OF THE INVENTION

Gram-negative bacteria that are resistant to aminoglycoside, β-lactam, and fluoroquinolone antibiotics are increasingly common. These bacteria are often only susceptible to the polymyxins and related peptides having antibacterial properties. As a result, there is renewed interest in the use of polymyxins for the treatment of multidrug-resistant Gram-negative bacterial infections in humans.

Peptides such as polymyxin B and the related colistin (polymyxin E) have been administered to humans as antibacterial agents. However, their use has been previously limited because of their toxicity.

Thus, there is a need for new peptide compounds having equivalent antibacterial properties to polymyxin B with an improved therapeutic index, as well as methods of manufacturing such antibacterial compounds.

SUMMARY OF THE INVENTION

The disclosure describes the antibacterial compound of Formula (Ia) having antibacterial activity:

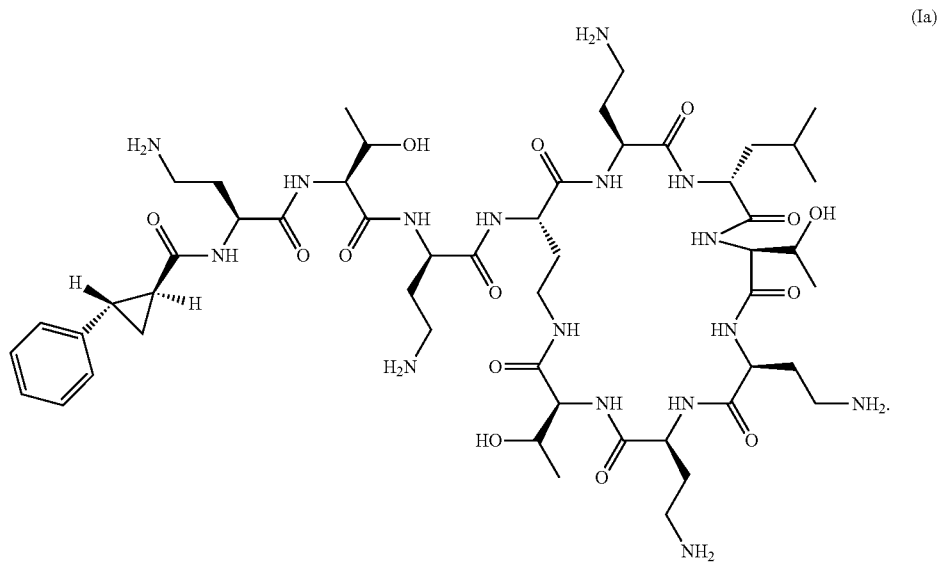 [SMILES: CC(C)C[C@H]1NC(=O)[C@H](CCN)NC(=O)[C@@H](NC(=O)[C@@H](CCN)NC(=O)[C@@H](NC(=O)[C@H](CCN)NC(=O)[C@H]2C[C@@H]2c2ccccc2)C(C)O)CCNC(=O)[C@H](C(C)O)NC(=O)[C@H](CCN)NC(=O)[C@H](CCN)NC(=O)[C@H](C(C)O)NC1=O]

(Ia)

Pharmaceutical compositions containing the antibacterial compound of Formula (Ia) are disclosed herein, as well as methods for preparing the antibacterial compound, amine-protected analogs of the antibacterial compound, and methods of using the antibacterial compound. The antibacterial compound of Formula (Ia) can be derived from a polymyxin such as polymyxin A. Pharmaceutical compositions comprising a compound of Formula (Ia), or a pharmaceutically acceptable salt and/or prodrug thereof, are useful, for example, in treating bacterial infections arising from Gram negative pathogens. Methods for treating an infection in a subject can include administering to the subject a therapeutically effective amount of a compound of Formula (Ia), or a pharmaceutically acceptable salt thereof. The antibacterial compounds can also be used in the manufacture of medicaments for treatment of infections.

BRIEF DESCRIPTION OF THE FIGURE

The FIGURE is a synthetic scheme depicting a method for preparing a compound of Formula (Ia) and other compounds.

DETAILED DESCRIPTION OF THE INVENTION

A description of example embodiments of the invention follows.

Definitions

As used herein and unless otherwise indicated, the following words, phrases and symbols shall have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom.

"Amino protecting group," as used herein, refers to any substituent that may be used to prevent an amino group on a molecule from undergoing a chemical reaction while chemical change occurs elsewhere in the molecule. An amino protecting group can be removed under the appropriate chemical conditions. Numerous amino protecting groups are well known to those skilled in the art, and examples of amino protecting groups, methods for their addition, and methods for their removal can be found in, for example, "Protective Groups in Organic Synthesis" by Theodora W. Greene and Peter G. M. Wuts, John Wiley and Sons, 3d Ed., New York, 1991, the relevant disclosure of which is incorporated herein by reference.

"Amino protecting group reagents," as used herein, refer to addition reagents that can react with an amino group such as the N-terminus of a peptide, thereby chemically modifying said amino group by addition of an amino protecting group.

As used herein to refer to an amino protecting group containing at least one "acidic substituent," the term "acidic substituent," refers to a portion of the amino protecting group (e.g., a substituent) containing a donatable hydrogen. Exemplary acidic substituents include the acid form of sulfo, sulfate, sulfonate, carboxy, carboxylate, phosphonate, and phosphate. In one embodiment, the protecting group comprises an aryl or heteroaryl substituted with an acidic substituent.

As used herein, the term "water-soluble" refers to a compound with sufficient water solubility for an intended purpose. Water-soluble compounds with an amino protecting group with an acidic substituent can have a first water solubility adequate to permit deacylation of such compounds in an aqueous medium (e.g., 0.1-5 g/L, preferably about 1 g/L or higher). Water-soluble antibiotic compounds can have a second water solubility adequate to permit dissolution of therapeutically effective amounts of the antibiotic compounds in an aqueous pharmaceutical composition (e.g., about 100-500 g/L, including at least about 300 g/L).

"Aryl," as used herein, refers to a mono-, bi-, or other multi-carbocyclic, aromatic ring system, including aromatic ring systems fused to one or more rings selected from aryl, cycloalkyl, and heterocyclyl, as well as aryl moieties having from 5-14 ring members. Nonlimiting examples of aryl groups include phenyl, naphthyl, biphenyl, and anthracenyl.

"Carboxy," as used herein, refers to a COOH radical.

"Fmoc" refers to a 9-fluorenylmethoxycarbonyl group.

"Halo," as used herein, refers to bromo, chloro, fluoro, and iodo, and the term "halogen" includes fluorine, chlorine, bromine, and iodine.

"Heteroaryl," as used herein, refers to mono-, bi-, or other multi-carbocyclic, aromatic ring systems wherein one to four carbon atom(s) has been replaced with one to four non-carbon atoms or hetero groups selected from O, N, NH, S, and SO. Heteroaryl ring systems can have, for example, five to fifteen ring members. Nonlimiting examples of heteroaryl groups include indolyl, pyridinyl, thiazolyl, thiadiazoyl, isoquinolinyl, pyrazolyl, oxazolyl, oxadiazolyl, triazolyl, and pyrrolyl groups.

"Polymyxin $B_1$" or "PMB," as used herein, refer to a compound of the following structural formula:

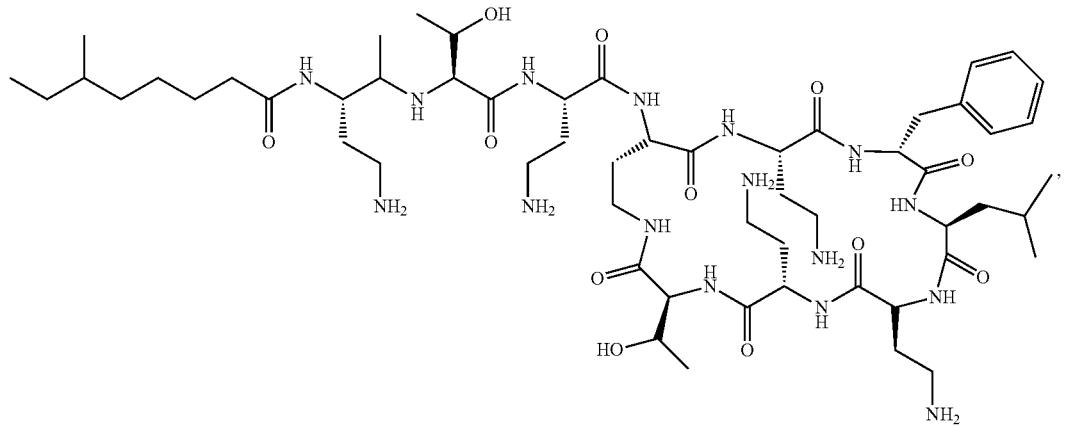

and commercially available salts thereof, such as a sulfate salt.

"Polymyxin A" and "PMA," as used herein, refer to a compound of the following structural formula:

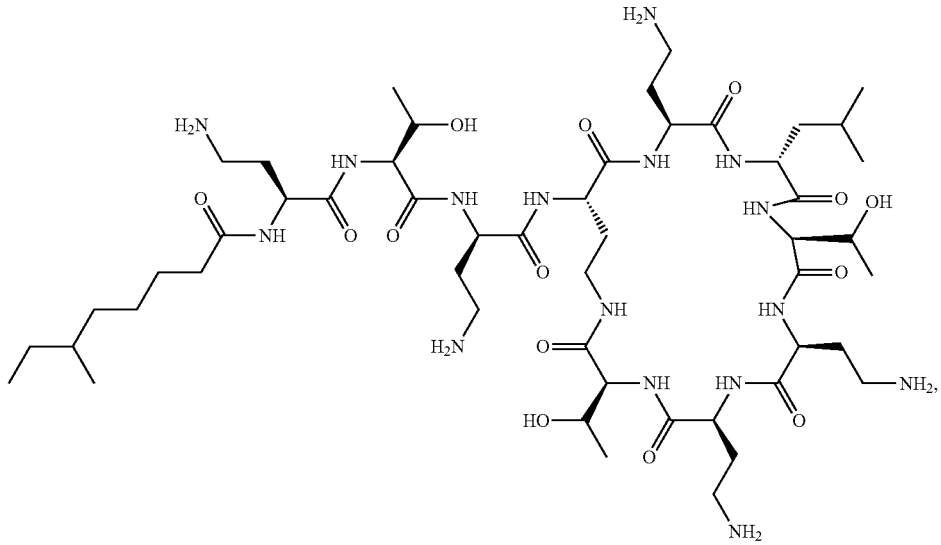 [SMILES: CCC(C)CCCCC(=O)N[C@@H](CCN)C(=O)N[C@H](C(=O)N[C@H](CCN)C(=O)N[C@H]1CCNC(=O)[C@H](C(C)O)NC(=O)[C@H](CCN)NC(=O)[C@H](CCN)NC(=O)[C@H](C(C)O)NC(=O)[C@@H](CC(C)C)NC(=O)[C@H](CCN)NC1=O)C(C)O]

and commercially available salts thereof, such as a sulfate salt.

The term "pharmaceutically acceptable prodrugs," as used herein, represents those prodrugs of compounds that are, within the scope of sound medical judgment, suitable for use in an intended therapeutic application (e.g., suitable for contact with the tissues of humans and lower animals) without undue toxicity, irritation, allergic response, commensurate with a reasonable benefit/risk ratio, and effective for their intended use. In one embodiment, the prodrug is an ester derivative of a compound of Formula (Ia). In another embodiment, the prodrug is a protected compound, such as a compound of Formula (IVd) in The FIGURE.

As used herein, the term "pharmaceutically acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically acceptable salts are well known in the art. In one embodiment of the invention, the pharmaceutically acceptable salt is a sulfate salt. For example, S. M. Berge, et al. describes pharmaceutically acceptable salts in J. Pharm. Sci., 1977, 66:1-19.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Pharmaceutically acceptable acidic/anionic salts also include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts.

Suitable pharmaceutically acceptable base addition salts include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine, arginine and procaine. All of these salts can be prepared by conventional means from the corresponding compound represented by the disclosed compound by treating, for example, the disclosed compounds with the appropriate acid or base. Pharmaceutically acceptable basic/cationic salts also include, the diethanolamine, ammonium, ethanolamine, piperazine and triethanolamine salts.

As used herein, the phrase "pharmaceutically acceptable carrier" refers generally to solvents, dispersion media, excipients, coatings, matrices, stabilizers, buffers, absorption enhancers, adjuvents, controlled release media, and the like, that are compatible with an intended use, such as pharmaceutical administration. The use of such carriers for pharmaceutically active substances is well known in the art. Nonlimiting examples of carriers include corn starch, gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

The term "therapeutically effective amount," as used herein, refers to an amount of an antibacterial compound that is effective to perform the function being sought by the researcher or clinician without unduly harming the tissues of the subject to which the agent is administered.

The term "subject," as used herein, refers to a mammal, a plant, a lower animal, or a cell culture. In one embodiment, a subject is a human or other animal patient in need of antibacterial treatment.

Unless otherwise indicated, the following abbreviations as used herein have the following meanings

| | |
|---|---|
| AUC = | area under the curve |
| ADME = | absorption, distribution, metabolism, excretion |
| BID = | bis in die, meaning to give medication twice a day |
| BUN = | blood urea nitrogen |
| cfu = | colony forming units |
| $CH_3CN$ = | acetonitrile |
| Cmax = | the maximum plasma concentration |
| CV = | cardiovascular |
| CYP = | Cytochrome P450 |
| EC50 = | half maximal effective concentration |
| ED = | effective dose |
| EDTA = | ethylenediaminetetraacetic acid |
| EtOH = | ethanol |
| HOAc = | acetic acid |
| HPLC = | high pressure liquid chromatography |
| MeOH = | methanol |
| MIC = | minimum inhibitory concentration to inhibit growth of the test organism |
| MIC90 = | MIC required to inhibit growth of 90% of the strains of an organism tested |
| MTD = | maximum tolerated dose |
| $NaH_2PO_4$ = | sodium phosphate |
| NOAEL = | no observable adverse effect level |
| PK = | pharmacokinetics |
| PMB = | polymyxin B |
| PME = | polymyxin E (colistin) |
| QD = | quaque die (every day) |
| TID = | ter in die, meaning to give medication three times a day |
| $OD_{600}$ = | optical density measured at 600 nm |

Antibacterial Compounds

Antibacterial compositions can include a compound of Formula (Ia) (also referred to herein as "Compound 5"):

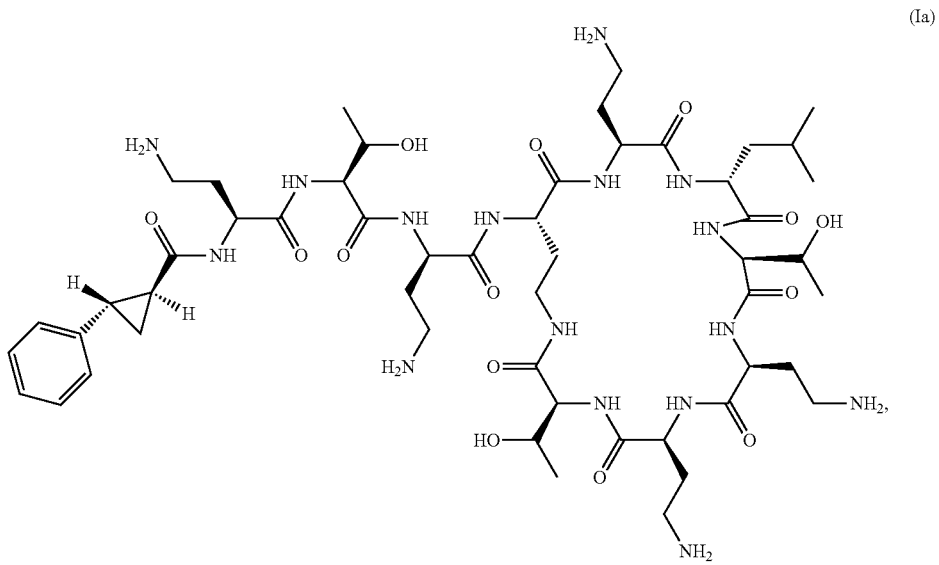 [SMILES: CC(C)C[C@H]1NC(=O)[C@H](CCN)NC(=O)[C@@H](NC(=O)[C@@H](CCN)NC(=O)[C@@H](NC(=O)[C@H](CCN)NC(=O)[C@H]2C[C@@H]2c2ccccc2)C(C)O)CCNC(=O)[C@H](C(C)O)NC(=O)[C@H](CCN)NC(=O)[C@H](CCN)NC(=O)[C@H](C(C)O)NC1=O]

as well as pharmaceutically acceptable prodrugs or pharmaceutically acceptable salts thereof.

Alternatively, a compound of Formula (Ia) can be contained in a mixture of diastereomers (S,S and R,R enantiomers) described by Formula (Ib) below:

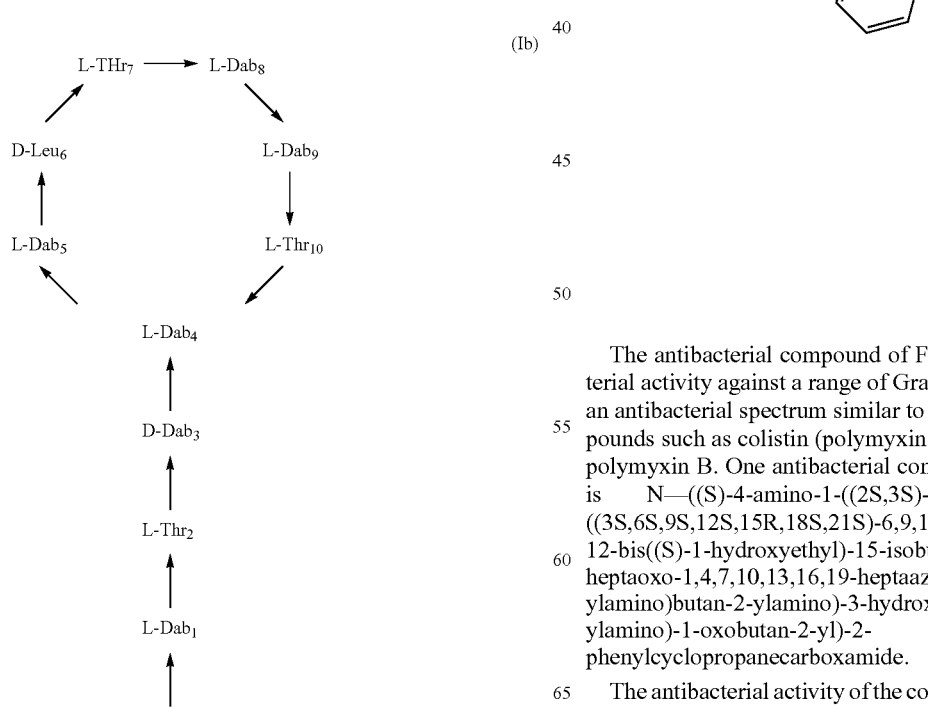

The antibacterial compound of Formula (Ia) has antibacterial activity against a range of Gram negative bacteria, and an antibacterial spectrum similar to certain polymyxin compounds such as colistin (polymyxin E), polymyxin A and/or polymyxin B. One antibacterial compound disclosed herein is N—((S)-4-amino-1-((2S,3S)-1-(R)-4-amino-1-oxo-1-((3S,6S,9S,12S,15R,18S,21S)-6,9,18-tris(2-aminoethyl)-3,12-bis((S)-1-hydroxyethyl)-15-isobutyl-2,5,8,11,14,17,20-heptaoxo-1,4,7,10,13,16,19-heptaazacyclotricosan-21-ylamino)butan-2-ylamino)-3-hydroxy-1-oxobutan-2-ylamino)-1-oxobutan-2-yl)-2-phenylcyclopropanecarboxamide.

The antibacterial activity of the compound of Formula (Ia), a comparator compound of Formula (II), and other compounds, are also described herein:

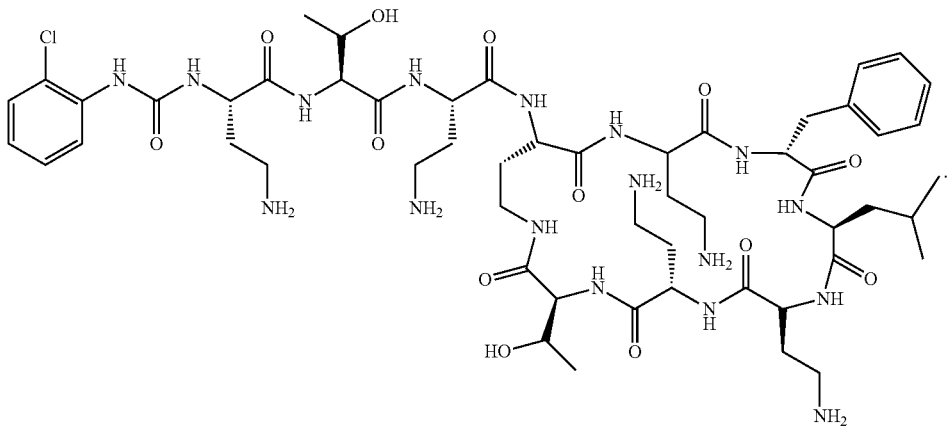

(II)

Synthesis of Compounds

The compound of Formula (Ia) can be prepared from a polymyxin starting material according to the synthetic scheme shown in The FIGURE. The compound of Formula (Ia) has antibacterial activity against various bacterial isolates that is comparable to the antibacterial activity of certain polymyxins (e.g., polymyxin A and polymyxin B) and the polymyxin derivative of formula (II).

The compound of Formula (Ia) can be obtained from any suitable lipopeptide starting material of Formula (III) comprising a cyclic portion with a plurality of 2,4-diaminobutanoic acid residues and an acyl exocyclic tail portion (T):

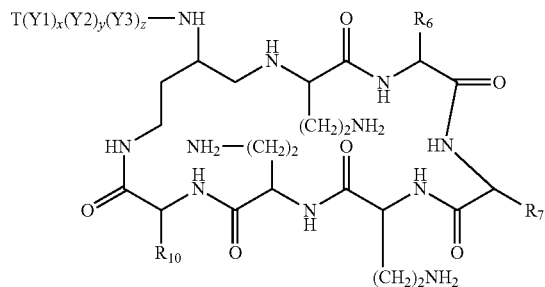

(III)

wherein Y1 and Y3 are each a 2,4-diaminobutanoic acid residue; Y2 is a threonine residue; x, y and z are integers independently equal to 1; $R_6$ is iso-butyl; $R_7$ and $R_{10}$ are 1-hydroxy-1-ethyl; T is R'—(C═O)—; and R' is an alkyl or (e.g., hydroxyl-)substituted alkyl, such as 6-methyloctanoyl, 6-methylheptanoyl, octanoyl, heptanoyl, nonanoyl, or 3-hydroxy-6-methyloctanoyl. Examples of suitable starting materials include polymyxin A. The starting material can be a naturally-occurring polymyxin compound isolated from the fermentation of *Bacillus polymyxa* according to procedures described in, e.g., Hausmann, et al. (1954) *J. Am. Chem. Soc.* 76, 4892-4896, the relevant teaching of which are incorporated by reference herein.

Referring to The FIGURE, the polymyxin A starting material (IVa) is reacted with an amino protecting group reagent (step (a)) to form a protected starting material (IVb) comprising an amino protecting group (PG) attached to the primary amino moieties in the starting material (IVa). Preferably, the amino protecting group (PG) comprises an acidic moiety to provide a protected starting material (IVb) that is sufficiently water-soluble to react with a deacylating agent in an aqueous medium (step (b)) to form a deacylated material (IVc). The deacylated material (IVc) can be reacted with an addition reagent (step (c)) to form a protected antibacterial compound (IVd). The amino protecting group (PG) can be removed from the protected antibacterial compound (IVd) (step (d)) to form a compound of Formula (I), including the compound of Formula (Ia).

The water solubility of the compounds of Formulae (IVa), (IVb), (IVc), (IVd) and Formula (Ia) may differ, each independently being suitable for different intended purposes. For example, a water-soluble protected starting material (e.g., compound of Formula (IVb) in The FIGURE) can include amino protecting groups with an acidic substituent (e.g., "PG" in Formula (IVb) in The FIGURE), providing sufficient water solubility to perform enzymatic deacylation (e.g., step (b) in The FIGURE) of the protected starting material at an acceptable yield in an aqueous medium. A product material can be an antibiotic compound of Formula (Ia) with sufficient water solubility to form an aqueous pharmaceutical composition comprising a therapeutically effective concentration of the compound of Formula (Ia).

The protecting group (PG) can be selected to provide a desired level of water solubility in the protected starting material (IVb). For example, the protecting group (PG) can include an aryl or heteroaryl moiety and at least one acidic substituent selected from carboxy, sulfo, sulfate, and salts thereof. Exemplary protecting groups include 9-fluorenylmethoxycarbonyl (Fmoc) substituted with acidic substituents or salts thereof, such as 2-sulfo-9-fluorenylmethoxycarbonyl ($HSO_3$-Fmoc), and its sodium salt ($NaSO_3$-Fmoc), 2-carboxymethyl-9-fluorenylmethoxycarbonyl (2-carboxymethyl-Fmoc), 2-carboxy-9-fluorenylmethoxycarbonyl (2-carboxy-Fmoc), and 4-carboxy-9-fluorenylmethoxycarbonyl (4-carboxy-Fmoc). Preferably, the protecting group is a sulfonic acid of 9-fluorenylmethoxycarbonyl, such as 2-sulfo-9-fluorenylmethoxycarbonyl. Additional amino protecting groups include, but are not limited to, the protecting groups disclosed in "Protective Groups in Organic Synthesis" by Theodora W. Greene, John Wiley and Sons, New York, 1991 at pp. 315-348, the relevant disclosure of which is incorporated herein by reference.

The protected starting material (IVb) can be reacted with an enzymatic deacylating agent in an aqueous medium to form the deacylated material (IVc). One example of a deacylating enzyme useful for deacylation of the protected starting material (IVb) is produced by certain microorganisms of the genus family Actinoplanaceae. Some of the known species and varieties of this family include *Actinoplanes philippinensis, Actinoplanes armeniacus, Actinoplanes utahensis, Actinoplanes missouriensis, Spirillospora albida,*

*Streptosporangium roseum, Streptosporangium vulgare, Streptosporangium roseum* var hollandensi, *Streptosporangium album, Streptosporangium viridialbum, Amorphosphorangium auranticolor, Ampullariella regularis, Ampullariella campanulata, Ampullariella lobata, Ampullariella digitata, Pilimelia terevasa, Pimelia anulata, Planomonospora parontospora, Planomonospora venezuelensis, Planobispora longispora, Planobispora rosea, Dactylosporangium aurantiacum*, and *Dactylosporangium thailandende*. All natural and artificial variants and mutants which are obtained from the Actinoplanacea family and which produce the enzyme may be used in this invention. The deacylating agent is preferably a polymyxin deacylase enzyme, which can be obtained from *Actinoplanes utahensis*.

The deacylase enzyme can be obtained as a water-soluble, freeze-dried solid. In one embodiment, the deacylase is obtained by fermenting *Actinoplanes utahensis*, separating the cells from the fermentation medium, washing the cells with water, extracting the cells with basic buffer at pH 8-11 for about 20 minutes, adjusting the extract to pH 7-8 and freeze-drying. The powdered form of the enzyme resulting from this process can be relatively stable and can be readily re-dissolved in water for use. Further purification can be obtained by gel filtration, membrane filtration or other types of chromatography. This enzyme can deacylate, for example, a sodium salt of N-[2-sulfo-9-fluorenylmethoxycarbonyl]$_5$ polymyxin A, to obtain the deacylated protected peptide having the Formula (IVc) in The FIGURE. In other embodiments, the enzyme from *Actinoplanes utahensis* can be used as the whole broth from the fermentation or as the washed cells.

The enzyme from *Actinoplanes utahensis* can also be used as a water-solubilized preparation. The water-solubilized enzyme preparation can be obtained by a relatively strong basic extraction of the washed cells, followed by adjustment of the pH of the clear extract to at least or about pH 7-8. This water-solubilized enzyme preparation can be freeze-dried to a solid form.

Referring to step (c) of The FIGURE, the deacylated material (IVc) is reacted with an addition reagent selected to react with a primary amino group at the N-terminus of the exocyclic portion of the deacylated material (IVc), thereby chemically modifying the amino group by addition of all, or a component of, the addition reagent to the amino group. For example, an addition reagent may be an acylamino reagent such as $R_1$—(C=O)-LG, wherein $R_1$ is defined in Table 1 of the Examples and LG is a leaving group. An addition reagent may also be, for example, an isocyanate, isothiocyanate, activated ester, acid chloride, sulfonyl chloride, activated sulfonamide, activated heterocycle, activated heteroaryl, chloroformate, cyanoformate, thioacylester, phosphoryl chloride, phosphoramidate, imidate, or lactone. An addition reagent may also be an aldehyde or ketone that reacts with an amine under reductive conditions to form an alkylated amine. An addition reagent may also be an activated amino acid, or an amino acid and a peptide coupling reagent, e.g., PyBOP® (benzotriazole-1-yl-oxy-tris-pyrrolidino-phosphonium hexafluorophosphate), HBtU (2-(1H-benzotriazole-1-yl)-1,1,3,3-tetramethyluronium hexafluorophosphate), HBtU/HOBt (2-(1H-benzotriazole-1-yl)-1,1,3,3-tetramethyluronium hexafluorophosphate/N-hydroxybenzotriazole), or DCC (dicyclohexylcarbodiimide). In the addition reaction shown in step (c) of The FIGURE, various addition reagents can be selected to reactively couple the substituent "$R_1$-" to the primary amine in the deacylated material (IVc) to form compounds of Formula (I), where $R_1$ is defined in Table 1 of the Examples.

The protected antibacterial compound (IVd) in the The FIGURE can be converted to a compound of Formula (I) by removing the protecting groups (PG) of the protected antibacterial compound (IVd) (e.g., by deprotection using standard methods such as those described in "Protective Groups in Organic Synthesis" by T. W. Green, John Wiley and Sons, New York, 1991, the relevant disclosure of which is incorporated herein by reference). As those skilled in the art will recognize, the choice of amino protecting group employed in the first step of the process (step (a)) will dictate the reagents and procedures used in removing said protecting group(s). In one embodiment of the invention, an organic base (e.g., cyclic amine base) can be used to perform the deprotection of protected antibacterial compound (IVd).

After removal of the amino protecting groups (PG), a compound of Formula (I) can be purified by gel filtration, chromatography, or reverse-phase high-performance liquid chromatography (HPLC). Diastereomers can be separated by conventional means such as chromatography or crystallization. Enantiomers can be obtained by resolution of the racemic mixtures according to conventional processes, for example by formation of diastereomeric salts by treatment with an optically active acid or base. Alternative processes for separation of enantiomers include the use of a chiral chromatography column optimally chosen to maximize the separation of the enantiomers, or the use of supercritical fluid chromatography (SFC). Optically active compounds can likewise be obtained by utilizing optically active starting materials. These isomers may be in the form of a free acid, a free base, an ester or a salt.

The "enantiomeric excess" or "% enantiomeric excess" of a composition can be calculated using the equation shown below:

$$ee = \left| \frac{R-S}{R+S} \right| \times 100\%$$

where R and S represent the respective fractions of each enantiomer in a mixture, such that R+S=1. When a single enantiomer is named or depicted by structure, the depicted or named enantiomer is present in an ee of at least or about 50%, about 60%, about 70%, about 80%, about 90%, about 95%, about 98%, about 99% or about 99.9%. In the example shown below, a composition contains 90% of one enantiomer, e.g., the S enantiomer, and 10% of the other enantiomer, i.e., the R enantiomer.

ee=(90−10)/100=80%.

Thus, a composition containing 90% of one enantiomer and 10% of the other enantiomer is said to have an enantiomeric excess of 80%. The enantiomeric excess of Compound 5 prepared according to the procedure detailed in Examples 2 and 3 was determined to be at least or about 94.4%.

Pharmaceutical Antibacterial Compositions

Pharmaceutical compositions can be formed by combining a compound of Formula (Ia) or a pharmaceutically acceptable prodrug or salt thereof, with a pharmaceutically acceptable carrier suitable for delivery to a recipient subject (e.g., a human) in accordance with known methods of drug delivery. Antibacterial pharmaceutical compositions suitable for administration of a compound of Formula (Ia) can be formulated. The compound of Formula (Ia), compounds of Formula (Ib), and/or pharmaceutically acceptable salts or prodrugs thereof can be included in a pharmaceutical antibacterial composition along with one or more carriers.

Compounds of Formula (Ia) and/or Formula (Ib) can be formulated as a variety of salts or prodrugs to improve stability or toxicological properties of the compound, increase or decrease solubility, improve pharmacokinetic performance of the compound (e.g., $C_{max}$ or AUC measurements) or improve storage properties (e.g., to reduce hygroscopicity) of a pharmaceutical composition. Pharmaceutically acceptable salts of a compound of Formula (Ia) may be prepared by conventional means from the corresponding compound of the invention by treating, for example, the compound with the appropriate acid or base. Examples of publications describing the selection and formation of pharmaceutically acceptable salts of medicinal compounds include Haynes, *Delia* A., et al., "Occurrence of Pharmaceutically Acceptable Anions and Cations in the Cambridge Structural Database," Journal of Pharmaceutical Sciences, v. 94, no. 10, 2111-2120 (October 2005), and Stahl, P H, et al., Eds., "Handbook of Pharmaceutical Salts Properties, Selection and Use," Weinheim/Zurich, Wiley-VCH/VHCA, the relevant teachings of which are incorporated herein by reference.

A compound of Formula (Ia) may also be formulated as a prodrug in a pharmaceutical composition. Prodrugs can include an antibacterial compound disclosed herein having one or more amino groups protected with $HSO_3$-Fmoc and/or other amino protecting groups comprising at least one acidic group (e.g., "PG" in compounds of Formulae (IVb-d) in The FIGURE). The $HSO_3$-Fmoc group can be cleaved after introduction into an animal, such as, e.g., a mammal, including a human, liberating the biologically active compound. Administration of a biologically active compound as the protected prodrug may result in a slow release mechanism for the antibacterial compound. Other suitable prodrugs can include esters of a compound of Formula (Ia). A discussion of prodrugs is provided in, e.g., Gershonov, et al. (2000), J. Med. Chem. 43: (13), 2530-2537, and Schechter, et al. (2002), J. Med. Chem. 45: (19), 4264-4270, the relevant teaching of which are incorporated by reference herein.

The pharmaceutical compositions can be formulated for suitable delivery, including intravenous, intramuscular, intraperitoneal, subcutaneous, intraocular, intrathecal, intraarticular, intrasynovial, cisternal, intrahepatic, intralesional and intracranial injection, infusion, and/or inhaled routes of administration for the therapeutic treatment of medical conditions, such as bacterial infections.

Pharmaceutical preparations can be prepared in accordance with standard procedures and are administered at dosages that are selected to treat infection (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of methods for administering various antimicrobial agents for human therapy).

The pharmaceutical composition can include one or more carriers, as defined above, for an intended medical use. Pharmaceutical compositions for parenteral injection comprise pharmaceutically acceptable aqueous or nonaqueous solutions of an antibacterial compound of Formula (Ia) in addition to one or more of the following: pH buffered solutions, adjuvants (e.g., preservatives, wetting agents, emulsifying agents, and dispersing agents), liposomal formulations, nanoparticles, dispersions, suspensions or emulsions as well as sterile powders for reconstitution into sterile injectable solutions or dispersions just prior to use. In one particular example, a pharmaceutical composition includes about 92-98% w/w of an active antibacterial component, such as a compound of Formula (Ia) and/or compounds of Formula (Ib), and about 0-3% (including about 0-1%, 0-3%, 1-3%, up to 1%, and/or up to 3%) w/w of a second active component, such as a compound of Formula (Ib), wherein the second active component is added to the other components of the pharmaceutical composition. One particular intravenous formulation is formed by combining an antibacterial active component with the remaining components of an intravenous pharmaceutical composition, where the active component is about 90-95% w/w of a compound of Formula (Ia) in a mixture of compounds of Formula (Ib) and about 0-1% w/w of other compounds. For intravenous (IV) use, the pharmaceutical composition can include any of the commonly used intravenous fluids that can be administered by infusion, such as physiological saline or Ringer's solution. Injectable depot forms to release the antibacterial agent in situ can be made by forming microencapsulating matrices of the drug in biodegradable polymers such as polylactide-polyglycolide. Depending on the ratio of drug to polymer and the nature of the particular polymer employed, the rate of drug release can be controlled. For intramuscular preparations, a sterile formulation of a compound of the present invention, or a suitable soluble salt form of the compound, for example the hydrochloride salt, can be dissolved and administered in a pharmaceutical diluent such as Water-for-Injection (WFI), physiological saline or 5% glucose.

In some cases, in order to prolong the effect of the drug, it may be desirable to slow the absorption of the drug following subcutaneous or intramuscular injection. This may be accomplished by the use of a liquid suspension of crystalline or amorphous material with poor water solubility. Amorphous material may be used alone or together with stabilizers as necessary. The rate of absorption of the drug then depends upon its rate of dissolution, which in turn, may depend upon crystal size and crystalline form.

The injectable formulations can be sterilized, for example, by filtration through a bacterial-retaining filter, or by incorporating sterilizing agents in the form of sterile solid compositions, which can be dissolved or dispersed in sterile water or other sterile injectable media just prior to use.

The pharmaceutical compositions can be in powder form for reconstitution in the appropriate pharmaceutically acceptable carrier at the time of delivery. In another embodiment, the unit dosage form of the compound can be a solution of the antibacterial compound of Formula (Ia)/(Ib), or a pharmaceutically acceptable salt thereof, in a suitable diluent in sterile, hermetically sealed ampoules or sterile syringes.

Methods of Using Antibacterial Compositions

The antibacterial compounds described herein are useful in the manufacture of antibacterial pharmaceutical compositions and the treatment of bacterial infections using these compositions. In particular, the antibacterial compounds are useful in treating (e.g., controlling, inhibiting and/or eliminating) Gram negative bacterial infections. Methods of treating bacterial infections in subjects (e.g., humans and animals) can include the administration of a therapeutically effective amount of an antibiotic compound of the Formula (Ia), or a pharmaceutically acceptable salt or prodrug thereof.

The antibacterial compound of Formula (Ia) can be used in vivo, for example, to treat bacterial infections in a subject, as well as in vitro, for example to treat cells (e.g., bacteria) in culture to eliminate or reduce the level of bacterial contamination of a cell culture. In one embodiment, a compound of Formula (Ia), or a composition thereof, is administered to a cell culture, such as by administering in a nutrient medium.

Methods of treatment of such infections include administering to a subject in need thereof a therapeutically effective amount of an antibacterial compound of Formula (Ia). The compound can be parenterally administered to a subject having or suspected to have a bacterial infection, such as a Gram negative bacterial infection.

The antibacterial compound of Formula (Ia) is preferably used in vivo to treat an infection in a subject by administering a therapeutically effective amount of a compound of Formula (Ia), or a pharmaceutically acceptable salt or prodrug thereof, in a pharmaceutical composition. The method can comprise parenterally administering to a subject in need thereof a pharmaceutical composition comprising a compound of Formula (Ia), or a pharmaceutically acceptable salt or prodrug thereof. Pharmaceutical compositions include compositions comprising a compound of Formula (Ia) in an amount sufficient to achieve the intended purpose, i.e., the treatment or prevention of a bacterial infection. The amount and concentration of antibacterial compound of Formula (Ia) in the pharmaceutical composition, as well as the quantity of the pharmaceutical composition administered to a subject, can be selected based on clinically relevant factors, such as medically relevant characteristics of the subject (e.g., age, weight, gender, other medical conditions, and the like), the solubility of the antibacterial compound in the pharmaceutical composition, the potency and activity of the antibacterial compound, and the manner of administration of the pharmaceutical composition. A pharmaceutical composition comprising a therapeutically effective amount of an antibacterial compound of Formula (Ia), or a pharmaceutically acceptable salt or prodrug thereof, can be administered intravenously to a patient for treatment of Gram negative infections in a clinically safe and effective manner, including one or more separate administrations of the composition. For example, about 0.05 mg/kg to about 5.0 mg/kg can be administered to a subject per day in one or more doses (e.g., doses of about 0.05 mg/kg QD, 0.10 mg/kg QD, 0.50 mg/kg QD, 1.0 mg/kg QD, 1.5 mg/kg QD, 2.0 mg/kg QD, 2.5 mg/kg QD, 3.0 mg/kg QD, 0.75 mg/kg BID, 1.5 mg/kg BID or 2.0 mg/kg BID). For certain antibiotic indications, the total daily dose of a compound of Formula (Ia) can be about 0.05 mg/kg to about 3.0 mg/kg of one or more compound of Formula (Ia) administered intravenously to a subject one to three times a day, including administration of total daily doses of about 0.05-3.0, 0.1-3.0, 0.5-3.0, 1.0-3.0, 1.5-3.0, 2.0-3.0, 2.5-3.0, and 0.5-3.0 mg/kg/day of a compound of Formula (Ia), and/or Formula (Ib) using 60-minute QD, BID or TID intravenous infusion dosing. In one particular example, antibiotic pharmaceutical compositions can be intravenously administered QD or BID to a subject with, e.g., total daily doses of 1.5 mg/kg, 3.0 mg/kg, 4.0 mg/kg of a composition with up to about 92-98% wt/wt of Formula (Ia). The amount per administered dose and the total amount administered will depend on factors such as the nature and severity of the infection, the age and general health of the patient, the tolerance of the patient to the compound and the microorganism or microorganisms involved in the infection.

The compound of Formula (Ia) can also be administered by inhalation. Pharmaceutical compositions comprising a compound of Formula (Ia), or a pharmaceutically acceptable salt or prodrug thereof, can be administered as an aerosol for the treatment of pneumonia or other lung-based infections. In one embodiment, the aerosol delivery vehicle is an anhydrous, liquid or dry powder inhaler. A compound of Formula (Ia) can be included in a pharmaceutical composition formulated for delivery as a dry powder or aerosol for nasal, sinunasal or pulmonary administration in a manner suitable for the prevention, management or treatment of airway infections.

In particular, the pharmaceutical compositions comprising antibacterial compound of Formula (Ia) can be used to treat a subject having a bacterial infection wherein the bacterial infection comprises, consists essentially of or consists of Gram-negative bacteria. These Gram-negative bacteria include, but are not limited to, *Acinetobacter* spp. (including *Acinetobacter baumannii*), *Citrobacter* spp., *Enterobacter* spp., *Escherichia* spp. (including *Escherichia coli*), *Pseudomonas aeruginosa*, *Klebsiella* spp. (including *Klebsiella pneumoniae*), *Salmonella* spp., *Shigella* spp., *Yersinia pseudotuberculosis*, and all species of *Enterobacter*, *Pasteurella*, *Brucella*, *Bordetella*, *Proteus*, *Serratia*, *Providencia*, and *Edwardsiella*. The bacteria infection can also be caused or exacerbated by a Gram-negative bacteria chosen from *Pseudomonas aeruginosa*, *Acinetobacter* spp, *Stenotrophomonas maltophilia*, *Escherichia coli*, *Klebsiella pneumoniae*, *Citrobacter* spp, and *Enterobacter*. In one embodiment, the compound of Formula (Ia) may be used to treat multiple drug resistant bacteria, such as Multiple Drug Resistant (MDR) *P. aeruginosa*, Extended Spectrum Beta Lactamase (ESBL) *K. pneumonia*, ESBL *E. coli*, and *A. baumannii*.

EXEMPLIFICATION

The pharmaceutical compositions can be used to treat a bacterial infection of any organ or tissue in the body caused by Gram-negative bacteria. These organs or tissue include, without limitation, skeletal muscle, skin, bloodstream, kidneys, heart, lung and bone. For example, a pharmaceutical composition comprising a compound of Formula (Ia), or a pharmaceutically acceptable salt or prodrug thereof, can be administered to a subject to treat, without limitation, skin and soft tissue infections (e.g., complex skin infections), bacteremia, interabdominal infections and urinary tract infections (e.g., cUTI). In addition, a compound of Formula (Ia), or a pharmaceutically acceptable salt or prodrug thereof, may be used to treat community acquired respiratory infections, including, without limitation, otitis media, sinusitis, chronic bronchitis and pneumonia (including community-acquired pneumonia, hospital-acquired pneumonia and ventilator associated pneumonia), including pneumonia caused by drug-resistant *H. influenzae*. A compound of Formula (Ia), or a pharmaceutically acceptable salt or prodrug thereof, can be administered to a subject to treat mixed infections that comprise different types of Gram-negative bacteria, or which comprise both Gram-positive and Gram-negative bacteria. These types of infections include intra-abdominal infections and obstetrical/gynecological infections. A compound of Formula (Ia), or a pharmaceutically acceptable salt or prodrug thereof, may also be administered to a subject to treat an infection including, without limitation, endocarditis, nephritis, septic arthritis, intra-abdominal sepsis, bone and joint infections and osteomyelitis. A compound of Formula (Ia), or a pharmaceutically acceptable salt or prodrug thereof, or a composition comprising a compound of Formula (Ia), or a pharmaceutically acceptable salt or prodrug thereof, may also be directly injected or administered into an abscess, ventricle or joint. The components of the pharmaceutical composition should be selected to provide an amount of the compound of Formula (Ia) that is greater than the relevant minimum inhibitory concentration (MIC) for bacteria at the target site. More preferably, it is selected to exceed the MIC by a factor of at least 2, or of at least 3, respectively.

EXAMPLES

A compound of Formula (Ia) (i.e., Polymyxin A decapeptide with a 2-phenylcyclopropane carboxamide (S,S isomer) tail) and a comparator compound of Formula (II) were prepared and tested.

Unless otherwise indicated, the antibacterial activities of compounds are indicated in the Examples as their minimum inhibitory concentrations (MICs) against *Pseudomonas aeruginosa*, *Abcinobacter Baubanni*, *Escherichia coli*, *Klebsiella pneumoniae*, *Citrobacter* spp, and *Enterobacter*. MICs can be determined by the conditions disclosed in the Examples, as well as those disclosed in Jarolmen, H. et al., "Activity of Minocycline Against R-Factor Carrying Enterobacteriaceae," Infectious Immunity, Vol. 1, No. 4, pp. 321-326, 1970, the relevant disclosure of which is incorporated herein by reference.

MIC's refer to the concentration of each antimicrobial agent required to inhibit the growth of a bacterial isolate, as well as the corresponding concentrations required to inhibit 50% and 90% of each group of microorganisms tested [$MIC_{50}$ and $MIC_{90}$, respectively, consistent with definitions in the "Instructions to Authors" for Antimicrobial Agents and Chemotherapy (Antimicrobial Agents and Chemotherapy, January 2010, p. 1-23, Vol. 54, No. 1, incorporated herein by reference)]. When only up to nine isolates of a species are tested, MIC's are reported as the MIC range of each antimicrobial agent tested. MIC values provided as numerical ranges for testing of a single bacterial strain indicate the range of MIC values obtained in repeated tests of the indicated bacteria strain.

Example 1

Preparation of the Deacylase

The deacylase was produced by culturing *Actinoplanes utahensis* NRRL 12052 under submerged aerobic fermentation conditions. The fermentation protocol employed is known (Boeck, L. D. et al., Journal of Antibiotics 41:(8), 1085-1092 (1998), incorporated herein by reference). A stock culture of the NRRL 12052 variant, preserved in 20% glycerol at −70° C., was introduced into a 25×150 mm test tube with a glass rod and Morton closure containing 10 mL of a medium composed of sucrose 2.0%, pre-cooked oatmeal 2.0%, distiller's grains and solubles 0.5%, yeast extract 0.25%, $K_2HPO_4$ 0.1%, KCl 0.05%, $MgSO_4.7H_2O$ 0.05% and $FeSO_4.7H_2O$ 0.0002% in deionized water. After incubation at 30° C. for 72 hours on a rotary shaker orbiting at 250 rpm the resulting mycelial suspension was transferred into 50 mL of PM3 medium in a 250 mL Erlenmeyer flask. This medium contained sucrose 2.0%, peanut meal 1.0%, $K_2HPO_4$ 0.12%, $KH_2PO_4$ 0.05% and $MgSO_4.7H_2O$ 0.025% in tap water. The flask was incubated at a temperature of 30° C. for a period of 60 to 90 hours. The harvest time was determined by an assay which involved HPLC analysis of the deacylation of N-[2-sulfo-9-fluorenlymethoxycarbonyl]$_5$ polymyxin B by the whole broth at different times during the fermentation.

Because single-colony isolates from a lyophile of the culture were heterogeneous for both morphology and enzyme production capability, selections were made to recover a stable, high-producing variant. Initially, multiple fermentations were carried out using inocula prepared from strain 12052. Vegetative growth from the flask yielding the best deacylating activity was plated on a differential agar (CM). CM agar contained corn steep liquor 0.5%, Bacto peptone 0.5%, soluble starch 1.0%, NaCl 0.05%, $CaCl_2.2H_2O$ 0.05% and Bacto agar 2.0%. Colonies were then selected for further evaluation. Isolate No. 18 was selected as a small colony type and shown to be the best deacylase producer of all colonies selected. Comparison was based on conversion of protected polymyxin B to deacylated protected polymyxin B as determined by HPLC. This isolate was routinely used for the production of the deacylase enzyme.

Example 2

Preparation of Compounds of Formulae Ia/Ib

Step (a): Preparation of Penta-9-(2-sulfo)fluorenyl-methoxycarbonyl-polymyxin A

Fluorenylmethoxycarbonyl N-hydroxysuccinimide (1.1982 g, 3.55 mmol) dissolved in 15 mL of methylene chloride was stirred in an ice bath, using a DrieRite tube to maintain a dry atmosphere. A solution of chlorosulfonic acid (0.21 mL, 3.15 mmol) in 6 mL of methylene chloride was added dropwise to give a yellow solution. The mixture was allowed to warm to room temperature and stirred for several hours. The resulting white precipitate was filtered and washed with cyclohexane-methylene chloride (1:1) then dried in vacuo over phosphorus pentoxide to afford 9-(2-sulfo)fluorenylmethoxycarbonyl-N-hydroxysuccinimide ($HSO_3$Fmoc-O-Su). Yield 1.148 g, (hygroscopic white solid). See, e.g., Y. Shechter et al. J. Med. Chem., 43, 2530 (2000).

Polymyxin A, as obtained from fermentation, was dissolved in a solution of 25 mL saturated sodium bicarbonate, 25 mL of water and 25 mL of tetrahydrofuran. A solution of 2-sulfo-9-fluorenylmethoxy-N-hydroxysuccinimide (2.0 g, 4.8 mmol) in 25 mL of tetrahydrofuran was added in several portions over 45 minutes. The reaction mixture was stirred at room temperature overnight then diluted with 50 mL of water. The reaction mixture was then acidified to pH 0.5-1 with approximately 30 mL of 6N hydrochloric acid to give an oily precipitate. The mixture was chilled overnight and the aqueous layer was decanted. The oily residue was dissolved in 100 mL of ethanol and the ethanol was evaporated in vacuo (35° C.) with the aid of ethyl acetate. The resulting solid was triturated with ethyl acetate, filtered and dried to afford 1.74 g of a mixture containing the protected polymyxin A products.

The above procedure can be used with the corresponding polymyxin A sulfate salt and 2-sulfo-9-fluorenylmethoxycarbonyl chloride with similar results.

Step (b): Deacylation of Penta-2-sulfo-9-fluorenylmethoxycarbonyl-polymyxin A

Penta-2-sulfo-9-fluorenylmethoxycarbonyl-polymyxin A (1 g) was dissolved in 800 mL of 0.02 M ammonium phosphate buffer (pH 7.2), combined with 200 mL EtOH and 7.44 g EDTA, and then adjusted to pH 8 with 1 N NaOH. The EtOH and EDTA were added to prevent some conversion to the protected nonapeptide and to act as a preservative. To this resulting solution was added 25 mg of deacylase enzyme and the reaction was run at pH 8 and stirred at 30° C. for 8-16 hours. The reaction was then adjusted to pH 6 with 1 N HCl and the protected polymyxin A decapeptide was added to the resin as described in the next section. The resulting filtrate contains the enzyme.

The completed 1 L deacylation reaction solution was adjusted to pH 6. Envi-Chrom P resin was added, the mixture was stirred for 1 hour, and the resin was removed by filtration. The resin was placed in a column, washed with 80 mL of 20% $CH_3CN$ in 0.02 M $NaH_2PO_4$ adjusted to pH 6.8 with approximately 40 mL of 22.5% $CH_3CN$ in the buffer and 80 mL of 25% $CH_3CN$ in the buffer. The deacylated protected compounds were then eluted from the resin with 40% $CH_3CN$ in the buffer as 8 mL fractions were collected. Fractions 4, 5, and 6 were combined, evaporated to remove $CH_3CN$, and the residual aqueous solution was freeze-dried to obtain 704 mg of crude product mixture. The crude product mixture was mixed with 20 mL of MeOH, stirred for 0.5 hours, and separated by centrifugation. The decant was evaporated to dryness, water was added to the residue, and the solution was freeze-dried to obtain 452 mg of deacylated protected compounds as a light tan powder. The product mixture contained about 85% of the deacylated protected decapeptide.

Step (c): Acylation of Deacylated Protected Decapeptide

The deacylated protected decapeptide (412 mg, approximately 0.16 mmol) was dissolved at room temperature in 4 mL of dimethylformamide (DMF) and 0.4 mL collidine/2M HCl (5:1 volume ratio) to yield a clear solution which was sampled for HPLC as O-time reaction reference. To the stirred solution was slowly added 80 µL (0.66 mmol) of activated trans-2-phenylcyclopropanecarboxylic acid (such as the HOBt ester). After stirring for 2-4 hours at room temperature, the reaction was sampled and analyzed by analytical HPLC and was found to contain approximately 100% conversion to the desired acylated protected intermediate.

Step (d): Deprotection of the Acylated Protected Compounds

To the reaction mixture in Step (c) was added 1.6 mL MeOH (to reduce mixture viscosity) and 0.4 mL piperidine to remove the protecting groups. The reaction mixture was diluted with 80 mL of Solvent A (see below) plus 0.28 mL HOAc (to ensure neutralization of excess piperidine), to yield a clear solution which contained the deprotected products, which were designated as Compound 5 and its isomer, Compound 6 (as shown in Table 1). Sample solutions (2 mg/mL in ethanol) were analyzed in triplicate (10 µL injections) using normal-phase, chiral HPLC. A Pirkle covalent (S,S) Whelk-01 5/100 Kromasil 25 cm column was used with an isocratic method. The mobile phase was 97:3 hexanes:ethanol, flowing at 2 mL/min for 10 min. The retention times listed in Table 1 were obtained using the above method with PDA detection, extracting data at 240 nm. Stereochemistry of the synthesized compounds was assigned by comparing retention times (RT) with those of known analytical standards.

TABLE 1

HPLC separation of the two isomers

| Source | Stereochemistry at cyclopropyl position | HPLC RT (min) |
|---|---|---|
| From Compound 6 | R/R | 5.153* |
| From Compound 5 | S/S | 4.272* |

*tail retention time

Example 3

Isolation and Purification of Compound of Formula (Ia)

Preparation of CM-Sepharose Cartridge

A carboxymethyl agarose (e.g. sold under the tradename, CM-SEPHAROSE) slurry (100 mL sample) was diluted with approximately 100 mL of 20% EtOH. Approximately 30 mL of the dilute slurry was poured into a 60 mL polypropylene solid phase extraction tube and the slurry was allowed to settle. The top frit was carefully put in place to exclude air bubbles to obtain final packing bed dimensions of 22×26.5 mm. The excess 20% EtOH was decanted and the packing was rinsed by gravity flow with 60 mL of Solvent A.

Product Isolation

The diluted reaction mixture was applied to the cartridge and allowed to flow in by gravity. The product-loaded cartridge was rinsed with 60 mL Solvent A and then rinsed with 24 mL of 0.05 M ammonium acetate at pH 5.0. The cartridge was stripped with 32 mL of 0.27 M sodium sulfate buffer (pH 2.3) (1:2 dilution of Stock Buffer A, see below). 4-mL fractions (#4 through #11) were collected and analyzed by HPLC to evaluate product content profile. Fractions 7 through 10 (containing approximately 99% of a mixture of compound 5 and compound 6) were pooled.

Purification by Preparative HPLC

The column was rinsed at room temperature at 10 mL/min with 100 mL each, in order, Eluent A, Eluent B, Eluent D and Eluent C. The pooled CM-Sepharose fractions were injected onto the column with two sequential injections, approximately 8 mL each, each being rinsed onto the column with 50 mL of Eluent C at 5.0 mL/min. The gradient was then initiated and all elutions were done at room temperature. The column eluate was monitored at 281 nm (approximately 1 cm flow cell path length). Fraction collection was initiated as Compounds 5 and 6 started to elute. 7.5-mL fractions were collected separately until the apex of the major peak followed by 3-mL fraction collection. Fractions were evaluated by analytical HPLC and the appropriate fractions were pooled.

Product Desalting and Freeze Drying

The desalting cartridge was prepared as follows: 2.0 g of EnviChrom-P styrene/divinylbenzene resin was slurried in 20 mL of 50% acetonitrile then poured into a 20 mL polypropylene cartridge. The top frit was put in place and the excess 50% acetonitrile was drained off. Using gravity flow for all subsequent steps, the packing was rinsed with 24 mL of 67% acetonitrile and then 24 mL of distilled water. Preparative HPLC fractions 14 through 29 were pooled and the acetonitrile was removed under vacuum at below 35° C. The desolventized fraction pool was applied to the cartridge and the loaded resin was rinsed with multiple 2 mL then 4 mL increments of distilled water (16 mL total). The desalted product was stripped from the resin using 48 mL of 67% acetonitrile. The acetonitrile was removed from the strip fraction under vacuum at below 35° C. and the aqueous solution was freeze dried to obtain 119 mg of Compound 5, which appeared to be pure by analytical HPLC. The preparative HPLC fractions containing Compound 6 were treated in a similar manner to obtain 15 mg of Compound 6, which also appeared pure by analytical HPLC.

Solvent A: 65% MeOH 0.04M ammonium acetate/0.02M acetic acid pH 5.0, 650 mL HPLC grade MeOH, 40 mL 1.00M ammonium acetate/0.50M acetic acid, pH 5.0 (1:10 dilution), and distilled water to 1.00 L.

Stock Buffer A: approximately 0.54 M in total sulfate (as sodium sulfate/bisulfate) pH 2.3 (1:10 dilution), 55.3 g (30 mL) concentrated sulfuric acid, 76.4 g (50 mL) 50% NaOH (approximately 20M), and distilled water to 1.00 L.

Preparative HPLC Conditions

Equipment: Waters Prep 4000 pump with Radial-Pak compression unit, Waters Delta-Pak C18 radial-pak cartridges (100 A pore, 2.5×21 cm), ABI 757 UV Detector with heat exchanger removed, 10 mL Loop injector, and Pharmacia fraction collector.

Eluent A: 100% isopropanol.
Eluent B: 20% isopropanol.
Eluent C: 15% acetonitrile 0.04M in sodium sulfate (pH 2.3), 150 mL acetonitrile, 80 mL Stock Buffer A, and distilled water to 1.00 L.
Eluent D: 30% acetonitrile 0.04M in sodium sulfate (pH 2.3) 300 mL acetonitrile, 80 mL Stock Buffer A, and distilled water to 1.00 L.

| Elution Gradient: | | | |
|---|---|---|---|
| Time (min) | % Eluent C | % Eluent D | Flow (mL/min) |
| 0 | 100 | 0 | 10.0 |
| 45 | 67 | 33 | 10.0 |
| 45.1 | 67 | 33 | 5.0* |

*Note: flow rate is reduced to accommodate limitation of fraction collector.

Example 4

Elucidation of the Chemical Structures of Formulae (Ia) and (Ib)

The C-terminal residue of Compound 5, threonine, is linked to the molecule via an amide bond on the α-amino side chain of 2,4-diaminobutyric acid, and the compound contains 10 amino acids which are 6 residues of 2,4-diaminobutyric acids, 3 residues of threonine, and one each of leucine. The compound has an average molecular weight of 1160.67 with an empirical formula of $C_{52}H_{88}N_{16}O_{14}$.

The structure shown in Formula (Ib) was deduced based on the method of synthesis from known starting materials and confirmed by HPLC and spectroscopic measurements.

Marfey's analysis of Compound 5 was conducted by reverse-phase HPLC combined with acid hydrolysis and derivatization with Marfey's reagent. Compound 5 contains 10 amino acids. The amino acid composition (ratio) of Compound 5 is as follows: threonine (3.0); 2,4-diaminobutyric acid (5.7); and leucine (1.1). The amount of 2,4-diaminobutyric acid residues in Compound 5 was found to be 5.7 residues, which is slightly less than the expected amount (6 residues). This result was consistent with the data from MS/MS analysis. One of the six 2,4-diaminobutyric acid residues, namely that at position 3, was determined to be in the D-configuration. The rest of the 2,4-diaminobutyric acid residues were determined to be in the L-configuration.

Nuclear magnetic resonance spectra were acquired at 5° C. on a 600 MHz instrument. One-dimensional spectra and two-dimensional COSY, TOCSY (mixing time 60 ms), NOESY (mixing time 150 ms), HSQC, HMBC were obtained for Compound 5 reference standard lot CG-01-003. The sample was dissolved in $D_2O$. The $^1H$, COSY, TOCSY and NOESY data were primarily used to assign $^1H$ peaks, while $^{13}C$, HSQC and HMBC were used to assign $^{13}C$ data, and to verify $^1H$ assignment. The sequential identification of residues in Compound 5 was executed through the analysis of two-dimensional NOESY spectra. Compound 5 exhibits NOE peaks from backbone NH of one residue to the side chain of the preceding residue which enables the sequential identification of residues.

Example 5A

In Vitro Biology of the Compound of Formula (Ia)

Antibacterial potency can be assessed by broth microdilution according to CLSI guidelines, plates can be incubated at 37° C., and aeration (rotation at 200 rpm) can be employed. In some assays, surfactant (Survanta, Abbott Laboratories) can be added to give a final concentration of 1, 10 and 40% in caMHB. Native polymyxin A, polymyxin B and the comparator compound of Formula II (polymyxin B decapeptide with an o-chlorophenyl urea tail) were included for comparison. In Tables 2A, 2B and 2C, "A" indicates a MIC value measurement that is the same as that observed for polymyxin B, "B" indicates a MIC value measured that is lower than the comparable value observed for polymyxin B, and "C" indicates a MIC value measured that is higher than the comparable value observed for polymyxin B.

TABLE 2A

MIC against the primary screening panel.

| Compound ID # | MIC micrograms/ml | | | | |
|---|---|---|---|---|---|
| | E. coli 1527 | K. pneumoniae 933 | P. aeruginosa 44 | A. baumannii 1570 | K. pneumoniae 1800 (PMX-resistant) |
| Polymyxin B | A | A | A | A | A |
| Formula (II) comparator | C | C | C | C | C |
| Native Polymyxin A | | B | A | C | C |
| Compound 5 | A | C | C | C | C |

TABLE 2B $MIC_{50-90}$ (micrograms/ml) against small panels (n = 35).

| Compound ID # | E. coli | | K. pneumoniae | | P. aeruginosa | | A. baumannii | |
|---|---|---|---|---|---|---|---|---|
| | $MIC_{50}$ | $MIC_{90}$ | $MIC_{50}$ | $MIC_{90}$ | $MIC_{50}$ | $MIC_{90}$ | $MIC_{50}$ | $MIC_{90}$ |
| Polymyxin B | A | A | A | A | A | A | A | A |
| Formula (II) comparator | C | C | C | C | B | A | C | C |
| Native Polymyxin A | B | A | C | C | A | C | A | A |
| Compound 5 | C | A | C | C | A | C | C | C |

TABLE 2C

MICs (micrograms/ml) for P. aeruginosa #44 in the presence of surfactant.

| Compound ID # | % surfactant | | |
|---|---|---|---|
| | 0% | 10% | 40% |
| Polymyxin B | 0.06 | 8 | >32 |
| Formula (II) comparator | C | B | A |
| Native Polymyxin A | C | B | B |
| Compound 5 | C | B | B |

Example 5B

Microbiology Studies

The potency and spectrum of Compound 5 was studied using a panel of Gram negative bacterial strains.

MIC testing can be performed according to Clinical and Laboratory Standards Institute (CLSI) M7-A7 (2006) broth microdilution methods. Unless otherwise indicated, MIC values are provided in units of micrograms per milliliter.

One day prior to testing, individual colonies were isolated by streaking onto rich, non-selective Tryptic Soy agar with 5% lysed sheeps blood (TSAB) with incubation at 35-37° C. for 18-24 hours.

Cultures were prepared by touching 3-5 colonies into 3 mL of cation-adjusted Mueller Hinton Broth (caMHB) in a 14-mL tube (caMHB was prepared and sterilized according to manufacturer's specifications). Cultures were grown at 37° C. and 200 rpm for approximately four hours prior to density adjustment for addition to the MIC assay.

$OD_{600}$ of growing cultures was measured and adjusted to approximately $10^5$ colony forming units per mL (CFU/mL) in caMHB for MIC inoculation (approximately $OD_{600}$ 0.001).

Diluted cultures were used to inoculate 50 μL per well in broth microdilution assays (final volume 100 μl per well; compounds were prepared in two-fold dilutions).

Plates were incubated 16-20 hours at 37° C., with shaking at 200 rpm.

$OD_{600}$ was determined for all wells. Growth was defined as $OD_{600}>0.1$. MICs were defined as the lowest concentration producing no visible turbidity ($OD_{600}<0.1$).

TABLE 3A

MIC$_{50}$ and MIC$_{90}$ for Compounds 5 and 6 (micrograms/mL).

| Compound No. | Structure | P. aeru MIC$_{50}$ | P. aeru MIC$_{90}$ | E. coli MIC$_{50}$ | E. coli MIC$_{90}$ | K. pneu MIC$_{50}$ | K. pneu MIC$_{90}$ | A. baum MIC$_{50}$ | A. baum MIC$_{90}$ |
|---|---|---|---|---|---|---|---|---|---|
| 1 | Polymyxin B | A | A | A | A | A | A | A | A |
| 2 | o-chlorophenyl urea | B | A | C | C | C | C | C | C |
|  |  | A | C | C | C | C | C | C | C |
| 3 | Polymyxin A | A | C | B | A | C | C | A | A |
| 4 | 4-chlorobenzyl carbamate on PMAD | A | A | C | A | A | C | B | B |
| 5 | trans-2-phenylcyclo-propane carboxamide on PMAD (isomer B) | A | C | C | A | C | C | C | C |

* some strains tested were multi-drug resistant

In Table 3A, the relative activity of each compound is shown in relation to polymyxin B (Compound 1): A indicates a measured MIC value equal to that of polymyxin B, B indicates a measured MIC value less than the corresponding MIC value measured for polymyxin B, and C indicates a measured MIC value greater than the corresponding MIC value measured for polymyxin B. Compound 5 showed in vitro activity and spectrum similar to that of polymyxin B (PMB). It was active against multi-drug resistant strains. Compound 5 was also active against E. coli, K. pneumonia, P. Aeruginosa and A. baumanni isolates.

Example 6

Mouse Thigh Infection Model In Vivo Pharmacology/Toxicology of Compound of Formula (Ia)

Compound of Formula (Ia) was tested in a murine thigh model. For the thigh model, female CD-1 mice were rendered neutropenic by IP injection on days −4 and −1 with 150 and 100 mg/kg cyclophosphamide, respectively. On day 0 mice were infected with 1×10$^7$ colony-forming units (cfu) of A. baumannii 1570 in one thigh muscle, and then administered compound SC in a dose ranging from 2 to 12 mg/kg at 1 and 6 hours post-infection. The ED$_{-3log10}$ was calculated by determining the dose that resulted in a 3-log reduction of bacterial cfu in the thigh tissue compared to the cfu from thigh tissue of mice dosed with water 24 hours post-infection.

The mouse lung model was run in the same manner as the thigh infection model, except that mice were infected IN with 1×10$^7$ cfu of P. aeruginosa 44 on day 0. Doses administered in the lung study ranged from 8 to 20 mg/kg. The ED$_{-3log10}$ was based on cfu determination from the lung tissue 24 hours post-infection.

ED$_{-3log10}$ of a compound of Formula (Ia) in neutropenic mouse lung (P. aeruginosa 44)=6.35 mg/kg, SC, BID×1d*. In this experiment, the comparator, polymyxin B (PMB), had an ED$_{-3log10}$ of >20 mg/kg SC, BID×1d. The ED$_{-3log10}$ of Native Polymixin A (PMA) was 16.22 mg/kg SC, BID×1d (PMB value in this experiment was 20.6 mg/kg SC, BID×1d. Historical data on a compound of Formula (II) have shown an ED$_{-3log10}$ of approximately 12 mg/kg.

Lungs cleared within one log$_{10}$ of limit of detection at 8 through 20 mg/kg dose levels using the compound of Formula (Ia). This was not observed for PMA or PMB and has been seen in limited instances across the polymyxin derivative series. This was not seen for PMA, PMB or a compound of Formula (II).

Example 7

Acute Toxicity Testing in Rats: In Vivo Pharmacology/Toxicology of Compound of Formula (Ia)

One female Sprague-Dawley rat was administered a 1 mg/kg dose of the test Compound 5. Clinical observations were taken immediately following the administration of compound and at 0.5, 1, 2 and 4 hours post-dose.

Acute (anaphylactoid) observations: At a dose of 1 mg/kg i.v., anaphylactoid response was observed in 1 female Sprague-Dawley rat. Immediately following the dose, signs included flushed ears, abnormal gait, hypoactivity and squinty eyes. By 0.5 hours, these signs diminished, but the rat remained hypoactive. By 1 hour, the rat had no clinical signs and appeared normal. Native PMA was tested in a similar experiment, and no clinical signs were observed at an IV dose of 1 mg/kg.

Example 8

Pharmacological Studies

Compound 5 was tested for efficacy in certain animal models with different Gram negative pathogens.

In Vivo Efficacy of Compound 5 Against Lung Infection in Mice

Infection was induced in normal immunocompetent or neutropenic mice by intranasal inoculation of P. aeruginosa #44. Compound 5, polymyxin B, colistin, imipenem or ciprofloxacin were administered subcutaneously at 1 and 6 hours post-infection. At 24 hours post-infection, mice were humanely euthanized and the lungs of the mice were removed, homogenized, serially diluted, and plated on agar, to quantitate the bacterial burden. Compound 5, polymyxin B, colistin, ciprofloxacin and imipenem were evaluated for their ability to decrease the bacterial burden from the lungs compared with water-treated control mice.

P. aeruginosa #44 were grown in cation adjusted Mueller Hinton Broth (caMHB) (catalog#B12322; Fisher Scientific, Pittsburgh, Pa.) at 37° C. MIC testing was performed according to Clinical and Laboratory Standards Institute [CLSI, formerly National Committee for Clinical Laboratory Standards (NCCLS), Wayne, Pa.] guidelines for broth microdilution.

All of the test compounds were dissolved in sterile water for administration by subcutaneous (sc) injection. To dissolve ciprofloxacin, 2N HCl was added to the solution in small amounts until the powder dissolved completely. A series of dilutions of test compounds were prepared in water.

In the lung infection model using *P. aeruginosa* #44 as the infecting organism, CD-1 mice were made neutropenic by intraperitoneal (i.p.) administration with 150 mg/kg cyclophosphamide on day −4, followed by a second i.p. dose of 100 mg/kg cyclophosphamide on day −1. On day 0, a diluted, exponential-phase growing culture of *P. aeruginosa* #44 corresponding to $1\times10^5$ or $2.5\times10^8$ CFU respectively, in 0.1 mL of sterile saline, was inoculated by the intranasal route in mice. Just prior to inoculation, mice were anaesthetized with 60 mg/kg pentobarbital, i.p. The actual concentration of bacteria in the inoculum was confirmed by determination of viable counts by dilution plating on tryptic soy agar plates. The number of CFU of bacteria was determined after an incubation of 16 hours at 37° C.

Groups of five mice were used for each dose of the test compounds and the vehicle (water) control group. Each group received s.c. injections of test compounds or vehicle at 1 hour post-infection, and then at 6 hours post-infection for a total of 2 doses. In each study, there were three to five dose groups per test compound.

Eighteen hours after the last injection, the mice were euthanized by asphyxiation with $CO_2$. The lungs were removed aseptically, homogenized in 4 mL of sterile, distilled water and dilution plated on tryptic soy agar plates to quantify bacterial CFU. The number of CFU of bacteria in lungs was determined after an incubation of 16 hours at 37° C. (the CFU per milliliter of homogenate).

The results were expressed as the geometric mean $\log_{10}$ CFU/mL±the standard deviation. The limit of detection was 10 CFU per mL of lung homogenate. Lungs were considered sterile when no CFU were detected on the agar. The efficacy of the test compounds was assessed by comparing the number of $\log_{10}$ CFU/mL measured in the infected and treated mice with control animals treated with water. The efficacy of Compound 5 was also compared with the positive comparator antibiotics polymyxin B, colistin, ciprofloxacin and imipenem-cilastatin.

Dose response curves of test compounds were generated for each isolate. Regression lines were generated in Microsoft Excel and used to calculate the dose expected to produce a 3 $\log_{10}$ reduction in bacterial count as compared to water-treated group [$ED_{-3log10}$ (mg/kg, sc, BID)].

MIC testing was performed according to CLSI (formerly NCCLS) guidelines for broth microdilution. MICs of the compounds against *P. aeruginosa* #44 are shown in Table 5.

TABLE 5

| MIC of Certain Compounds against *P. aeruginosa* #44. | |
|---|---|
| Compound | MIC (micrograms/ml) against *P. aeruginosa* #44 In polystyrene plate |
| Compound 5 | 1-2 |
| Colistin | 2-4 |
| Polymyxin B | 1-2 |
| Imipenem-Cilastatin | 1-2 |
| Ciprofloxacin | 0.25 |

The teachings of all patents, published applications and references cited herein are incorporated by reference in their entirety.

While some embodiments have been shown and described, various modifications and substitutions may be made thereto without departing from the spirit and scope of the invention. For example, it is not intended that the claims set forth hereinafter be construed narrower that the literal language thereof, nor is it intended that exemplary embodiments from the specification be read into the claims.

Accordingly, it is to be understood that the present invention has been described herein by way of illustration only, and that such descriptions do not constitute limitations on the scope of the claims.

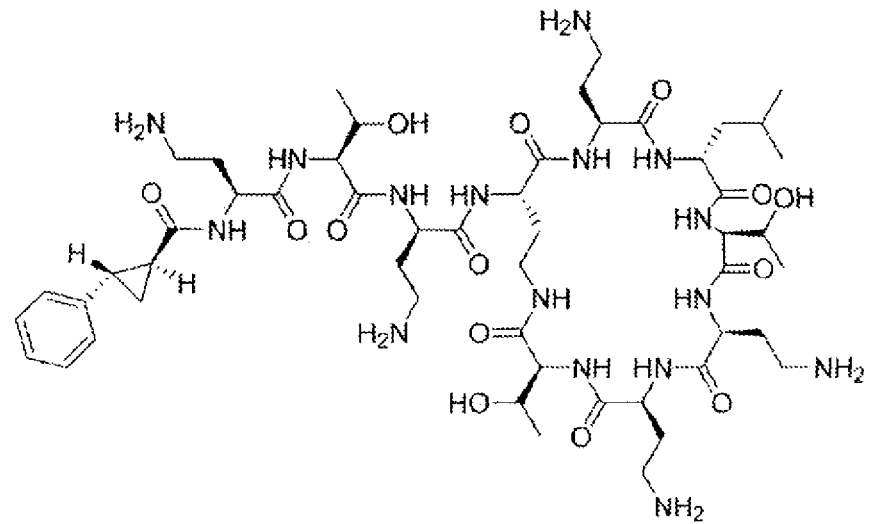

What is claimed is:

1. A pharmaceutical composition comprising an antibacterial compound of the Formula (Ia):

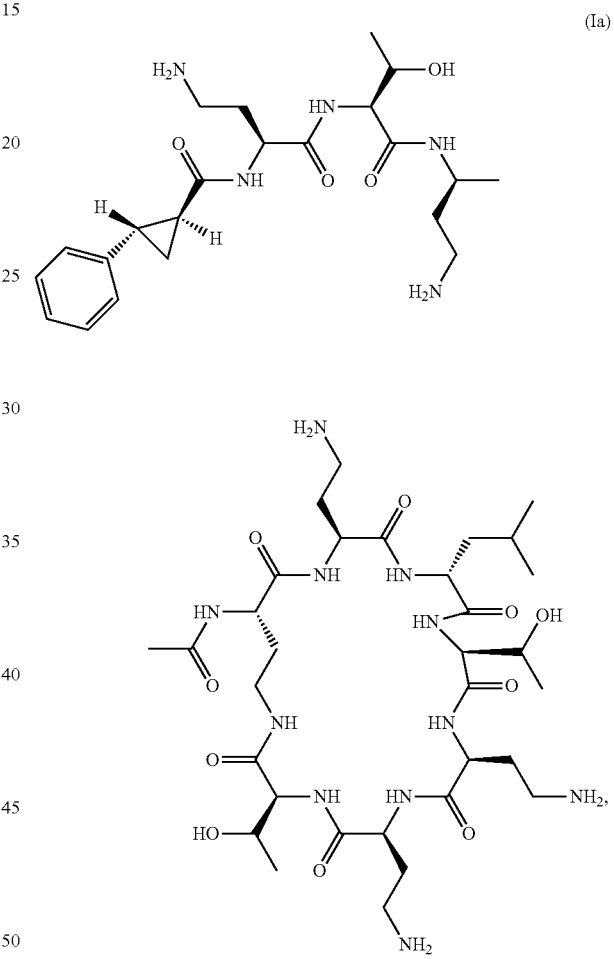

or a pharmaceutically acceptable salt thereof.

2. The composition of claim 1, further comprising a pharmaceutically acceptable carrier.

3. The composition of claim 2, wherein the composition is adapted for inhalation or intravenous administration.

4. The composition of claim 1, wherein the compound of Formula (Ia) is at least 94% enantiomerically pure.

5. A method of treating a bacterial infection comprising gram-negative bacteria, the method comprising administering to a subject in need thereof a therapeutically effective amount of a pharmaceutical composition comprising a compound of Formula (Ia):

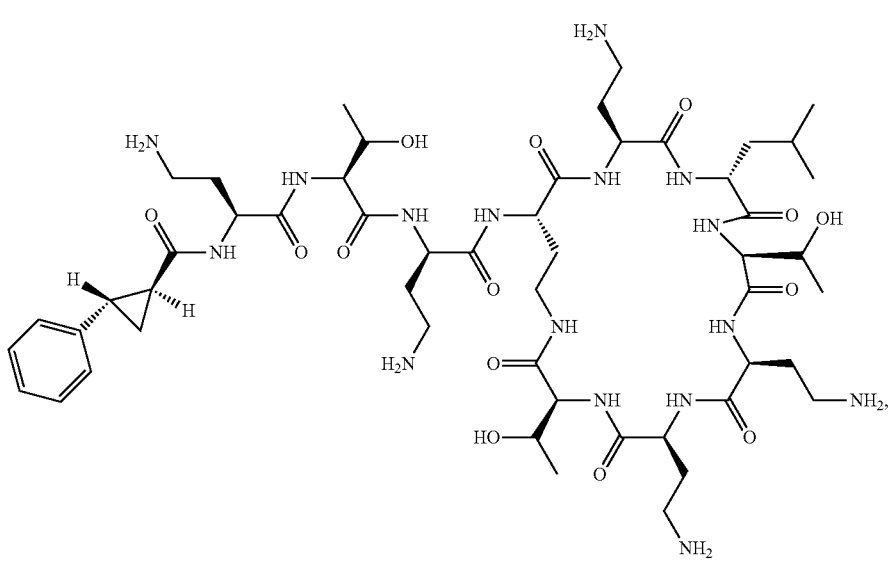

(1a)

or a pharmaceutically acceptable salt thereof.

6. The method according to claim 5, wherein the subject is a human, an animal, a cell culture, or a plant.

7. The method according to claim 5, further comprising the step of determining the species of gram-negative bacteria in the bacterial infection.

8. The method according to claim 5, wherein the bacterial infection comprises a susceptible or multi-drug resistant bacteria.

9. The method of claim 5, wherein the bacterial infection comprises *Pseudomonas aeruginosa, Acinetobacter* spp, *Stenotrophomonas maltophilia, Escherichia coli, Klebsiella pneumoniae, Citrobacter* spp, *Enterobacter* spp, or a combination thereof.

10. A process for preparing an antibacterial compound, the process comprising:
   a) treating polymyxin A with an amino protecting group comprising at least one acidic substituent to form a protected compound;
   b) treating the protected compound with a deacylating agent, to form at least one deacylated protected compound;
   c) treating the at least one deacylated protected compound with an activated ester to form at least one acylated protected compound; and
   d) treating the at least one acylated protected compound with an organic base to form an antibacterial compound having Formula (Ia):

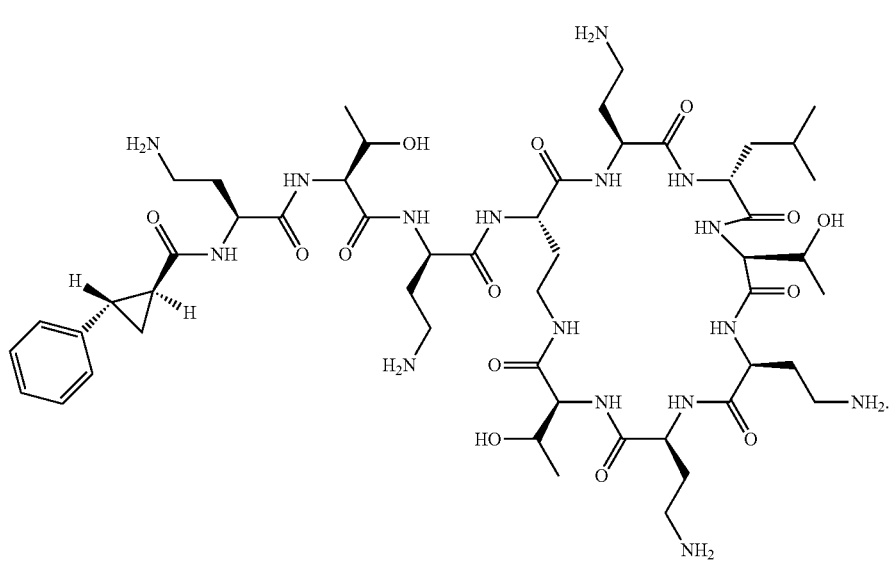

(1a)

11. The process of claim 10, wherein the deacylating agent is produced by *Actinoplanes utahensis*.
12. The process of claim 10, wherein the protecting group is 2-sulfo-9-fluorenylmethoxycarbonyl.
13. A compound represented by the Structural Formula (Ia):
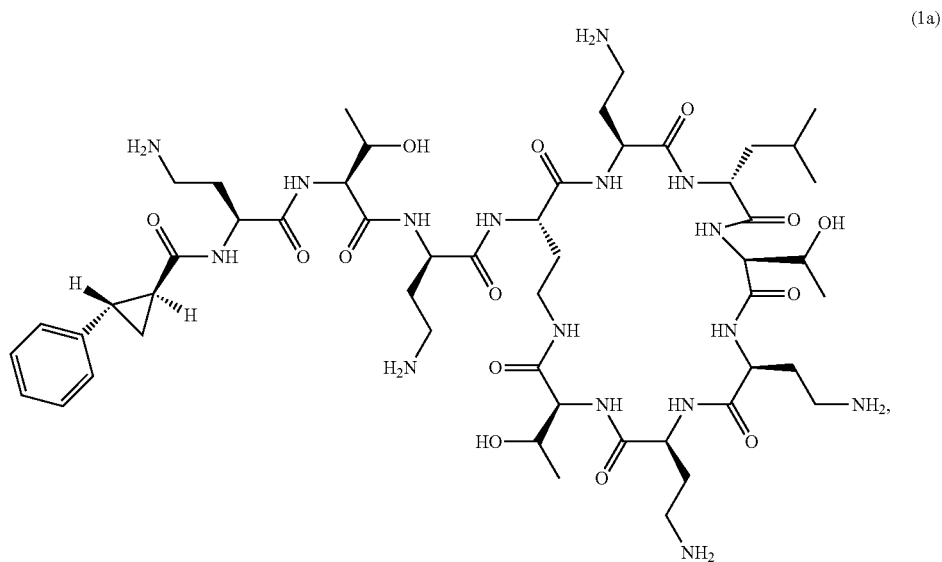 [SMILES: CC(C)C[C@H]1NC(=O)[C@H](CCN)NC(=O)[C@@H](NC(=O)[C@@H](CCN)NC(=O)[C@@H](NC(=O)[C@H](CCN)NC(=O)[C@H]2C[C@@H]2c2ccccc2)C(C)O)CCNC(=O)[C@H](C(C)O)NC(=O)[C@H](CCN)NC(=O)[C@H](CCN)NC(=O)[C@H](C(C)O)NC1=O]
(1a)
or a salt thereof.
* * * * *

UNITED STATES PATENT AND TRADEMARK OFFICE
CERTIFICATE OF CORRECTION

Page 1 of 3

PATENT NO.         : 8,415,307 B1
APPLICATION NO.    : 13/167495
DATED              : April 9, 2013
INVENTOR(S)        : William V. Curran et al.

It is certified that error appears in the above-identified patent and that said Letters Patent is hereby corrected as shown below:

In the Specifications:

In Columns 3 and 4, lines 23-39, please delete the existing formula and insert the following formula:

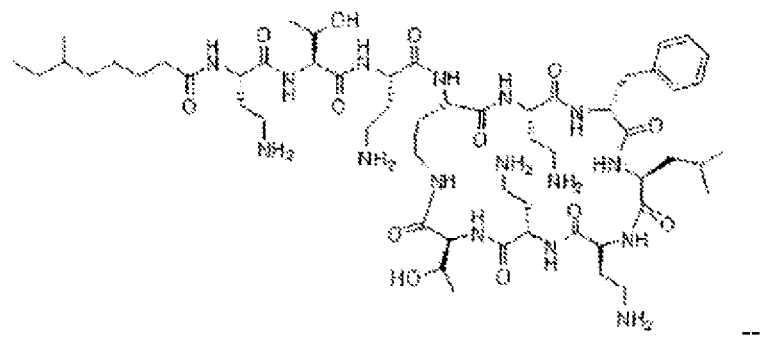

Signed and Sealed this
Eighteenth Day of June, 2013

Teresa Stanek Rea
*Acting Director of the United States Patent and Trademark Office*

CERTIFICATE OF CORRECTION (continued)
U.S. Pat. No. 8,415,307 B1

In Column 7, lines 33-65 and column 8, lines 33-50, please delete the existing formulas and insert the following formula:

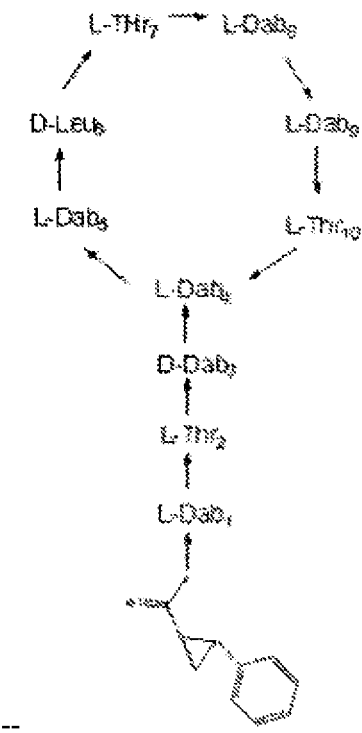

--                                                                              --

In Columns 9 and 10, lines 1-20, please delete the existing formula and insert the following formula:

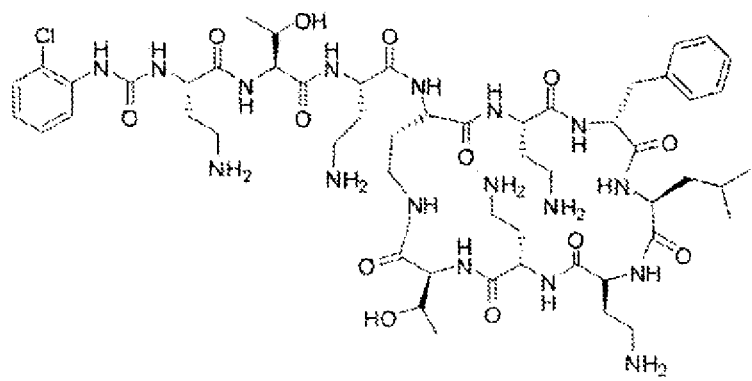

--                                                                              --

CERTIFICATE OF CORRECTION (continued)
U.S. Pat. No. 8,415,307 B1

In Column 9, lines 36-46, please delete the existing formula and insert the following formula:

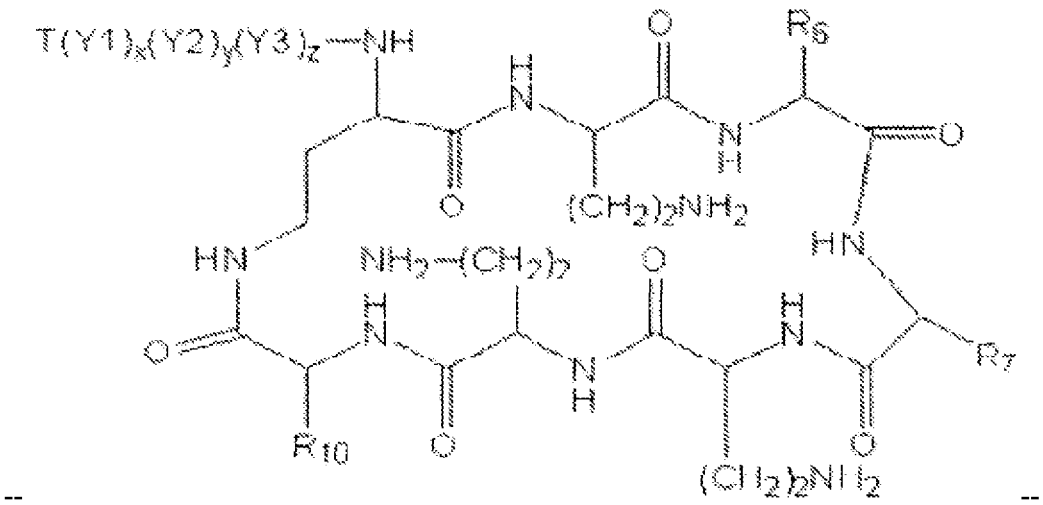

In the Claims:

In Column 26, lines 16-50, in Claim 1, please delete the existing formula and insert the following formula: